(12) United States Patent
Karim et al.

(10) Patent No.: US 7,674,850 B2
(45) Date of Patent: Mar. 9, 2010

(54) HARDENABLE SELF-SUPPORTING STRUCTURES AND METHODS

(75) Inventors: Naimul Karim, Maplewood, MN (US); Todd D. Jones, St. Paul, MN (US); Kevin M. Lewandowski, Inver Grove Heights, MN (US); Duane D. Fansler, Dresser, WI (US); James M. Nelson, Roseville, MN (US); Marcelino Salviejo-Rivas, Eagan, MN (US); Babu N. Gaddam, Woodbury, MN (US); Ahmed S. Abuelyaman, Woodbury, MN (US); Sumita B. Mitra, West St. Paul, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 1120 days.

(21) Appl. No.: 10/219,398

(22) Filed: Aug. 15, 2002

(65) Prior Publication Data

US 2003/0114553 A1    Jun. 19, 2003

Related U.S. Application Data

(60) Provisional application No. 60/312,355, filed on Aug. 15, 2001.

(51) Int. Cl.
C08K 3/34 (2006.01)

(52) U.S. Cl. .................. 524/493; 433/115; 433/116; 433/167; 433/218; 433/222.1; 433/228.1

(58) Field of Classification Search .......... 523/115, 523/116; 433/167, 218, 222.1, 228.1, 115, 433/116; 524/493
See application file for complete search history.

(56) References Cited

U.S. PATENT DOCUMENTS

| | | |
|---|---|---|
| 622,068 A | 3/1899 | Payne |
| 1,864,365 A | 6/1932 | Montgomery |
| 2,271,454 A | 7/1942 | Erdle et al. |
| 2,310,448 A | 2/1943 | Leib |
| 2,332,537 A | 10/1943 | Slatis |
| 2,551,812 A | 5/1951 | Nelson |
| 3,390,458 A | 7/1968 | Lytton |
| 3,541,068 A | 11/1970 | Taylor |
| 3,597,389 A | 8/1971 | Taylor |
| 3,997,637 A | 12/1976 | Rogers |
| 4,071,424 A | 1/1978 | Dart et al. |
| 4,080,412 A | 3/1978 | Colpitts et al. |
| 4,113,499 A | 9/1978 | Ivanov et al. |
| 4,115,488 A | 9/1978 | Colpitts |
| 4,129,946 A | 12/1978 | Kennedy |
| 4,278,630 A | 7/1981 | Scheicher |
| 4,347,888 A | 9/1982 | Butler |
| 4,503,169 A | 3/1985 | Randklev |
| 4,507,466 A | 3/1985 | Tomalia et al. |
| 4,514,174 A | 4/1985 | Dougherty et al. |
| 4,558,120 A | 12/1985 | Tomalia et al. |
| 4,568,737 A | 2/1986 | Tomalia et al. |
| 4,571,188 A | 2/1986 | Hamilton |
| 4,587,329 A | 5/1986 | Tomalia et al. |
| 4,631,337 A | 12/1986 | Tomalia et al. |
| 4,642,126 A | 2/1987 | Zador et al. |
| 4,648,843 A | 3/1987 | Mitra |
| 4,652,274 A | 3/1987 | Boettcher et al. |
| 4,694,064 A | 9/1987 | Tomalia et al. |
| 4,695,251 A | 9/1987 | Randklev |
| 4,713,975 A | 12/1987 | Tomalia et al. |
| 4,718,849 A | 1/1988 | Von Weissenfluh et al. |
| 4,737,550 A | 4/1988 | Tomalia |
| 4,767,331 A | 8/1988 | Hoe |
| 4,772,530 A | 9/1988 | Gottschalk et al. |
| 4,776,795 A | 10/1988 | Hornig |
| 4,778,386 A | 10/1988 | Spiry |
| 4,857,599 A | 8/1989 | Tomalia et al. |
| 4,871,779 A | 10/1989 | Killat et al. |
| 4,874,450 A | 10/1989 | Gottschalk |
| 4,954,414 A | 9/1990 | Adair et al. |
| 5,024,790 A | 6/1991 | Grossman et al. |
| 5,055,372 A | 10/1991 | Shanklin et al. |
| 5,057,393 A | 10/1991 | Shanklin et al. |
| 5,063,255 A | 11/1991 | Hasegawa et al. |
| 5,066,231 A * | 11/1991 | Oxman et al. ............ 433/214 |
| 5,135,545 A | 8/1992 | Pyzik et al. |
| 5,403,188 A | 4/1995 | Oxman et al. |
| 5,418,301 A | 5/1995 | Hult et al. |

(Continued)

FOREIGN PATENT DOCUMENTS

CA    1117685    2/1982

(Continued)

OTHER PUBLICATIONS

ANSI/ADA, American National Standard/American Dental Association, Specification No. 27; "Resin-Based Filling Material;" Council on Dental Materials, Instruments and Equipment, American Dental Association; Chicago, IL; 36 pgs. total (Jul. 16, 1993).
Plate et al., "Comb-Like Polymers, Structure and Properties,"*Journal of Polymer Science, Macromolecular Reviews*, vol. 8, Title page, Publication and Table of Contents page, and pp. 117-253 (1974).
Product Directions for Use and Material Safety Data Sheet, "Triad® Visible-Light Cure Provisional Material Directions for Use," Dentsply Trubyte, York, PA, 6 pgs. (Jun. 1997).
Product Directions for Use, "SureFil™ High Density Posterior Restorative," entsply Caulk, Dentsply, International, Inc., Milford, DE, 5 pgs. (Oct. 1998).
Product Directions for Use, "REVOTEK LC Light-Cured Resin For Temporary Crown & Bridge," GG Dental Products Corp., Alslo, IL, 5 pgs. (Nov. 2000).

(Continued)

*Primary Examiner*—Kriellion A Sanders

(57) ABSTRACT

Compositions, particularly for forming dental products, having a hardenable self-supporting structure with sufficient malleability to be subsequently customized into a second shape and then hardened, and methods.

64 Claims, 2 Drawing Sheets

U.S. PATENT DOCUMENTS

| | | | |
|---|---|---|---|
| 5,487,663 A | 1/1996 | Wilson | |
| 5,538,129 A | 7/1996 | Chester et al. | |
| 5,545,676 A | 8/1996 | Palazzotto et al. | |
| 5,552,177 A | 9/1996 | Jacobs et al. | |
| 5,635,545 A | 6/1997 | Oxman et al. | |
| 5,636,736 A | 6/1997 | Jacobs et al. | |
| 5,707,236 A | 1/1998 | Swanson et al. | |
| 5,753,781 A | 5/1998 | Oxman et al. | |
| 5,775,913 A | 7/1998 | Updyke et al. | |
| 5,785,178 A | 7/1998 | Kvitrud et al. | |
| 5,827,063 A | 10/1998 | Greenstein | |
| 5,830,986 A | 11/1998 | Merrill et al. | |
| 5,859,148 A | 1/1999 | Borggreve et al. | |
| 5,876,209 A | 3/1999 | Letcher | |
| 5,914,185 A | 6/1999 | Shoher et al. | |
| 5,919,870 A | 7/1999 | Letchford et al. | |
| 5,951,294 A | 9/1999 | Pierson | |
| 5,975,906 A | 11/1999 | Knutson | |
| 6,057,383 A | 5/2000 | Völkel et al. | |
| 6,084,004 A | 7/2000 | Weinmann et al. | |
| 6,114,409 A | 9/2000 | Krebber | |
| 6,121,344 A | 9/2000 | Angeletakis et al. | |
| 6,126,922 A | 10/2000 | Rozzi et al. | |
| 6,127,450 A | 10/2000 | Angeletakis | |
| 6,186,790 B1 | 2/2001 | Karmaker et al. | |
| 6,187,836 B1 | 2/2001 | Oxman et al. | |
| 6,196,840 B1 | 3/2001 | Zentz et al. | |
| 6,252,014 B1 | 6/2001 | Knauss | |
| 6,283,755 B1 | 9/2001 | Bergstrom | |
| 6,300,390 B1 | 10/2001 | Angeletakis | |
| 6,345,984 B2 | 2/2002 | Karmaker et al. | |
| 6,353,040 B1 | 3/2002 | Subelka et al. | |
| 6,359,090 B1 | 3/2002 | Angeletakis | |
| 6,382,980 B1 | 5/2002 | Shoher et al. | |
| 6,384,106 B1 | 5/2002 | Angeletakis | |
| 6,395,803 B1 | 5/2002 | Angeletakis | |
| 6,448,301 B1 | 9/2002 | Gaddam et al. | |
| 6,488,503 B1 | 12/2002 | Lichkus et al. | |
| 6,506,816 B1 * | 1/2003 | Ario et al. | 523/116 |
| 6,572,693 B1 * | 6/2003 | Wu et al. | 106/35 |
| 6,592,369 B2 | 7/2003 | Sun et al. | |
| 6,696,507 B2 | 2/2004 | Subelka et al. | |
| 6,790,035 B2 | 9/2004 | Tricca et al. | |
| 6,846,181 B2 | 1/2005 | Karmaker et al. | |
| 6,884,073 B2 | 4/2005 | Chilibeck | |
| 7,114,951 B2 | 10/2006 | Sun et al. | |
| 7,175,433 B2 | 2/2007 | Sun et al. | |
| 2002/0061493 A1 | 5/2002 | Sun et al. | |
| 2002/0086266 A1 | 7/2002 | Karmaker et al. | |
| 2002/0102519 A1 | 8/2002 | Baum et al. | |
| 2002/0117393 A1 | 8/2002 | Sun et al. | |
| 2003/0114553 A1 | 6/2003 | Karim et al. | |
| 2003/0153645 A1 | 8/2003 | Sun et al. | |
| 2003/0203339 A1 | 10/2003 | Chilibeck | |
| 2004/0005277 A1 | 1/2004 | Willison et al. | |
| 2004/0084792 A1 | 5/2004 | Sun et al. | |
| 2004/0224283 A1 | 11/2004 | Sun et al. | |
| 2005/0042576 A1 | 2/2005 | Oxman et al. | |
| 2005/0100868 A1 | 5/2005 | Karim et al. | |
| 2005/0147944 A1 | 7/2005 | Karim et al. | |
| 2006/0052470 A1 | 3/2006 | Grech et al. | |
| 2007/0018346 A1 | 1/2007 | Sun et al. | |
| 2009/0032989 A1 | 2/2009 | Karim et al. | |

FOREIGN PATENT DOCUMENTS

| | | |
|---|---|---|
| DE | 2751057 | 6/1981 |
| DE | 299 21 182 U1 | 5/2000 |
| DE | 19924116 | 1/2001 |
| EP | 0173567 A2 | 3/1986 |
| EP | 0 284 991 A2 | 10/1988 |
| EP | 0 284 991 A3 | 10/1988 |
| EP | 0970680 A2 | 1/2000 |
| EP | 1 138 272 A1 | 10/2001 |
| FR | 2 857 668 A1 | 1/2005 |
| JP | 46-040107 | 11/1971 |
| JP | 64-006204 | 1/1989 |
| JP | 2-138106 | 5/1990 |
| JP | 03-504874 | 10/1991 |
| JP | 4-183737 | 6/1992 |
| JP | 07-316391 | 12/1995 |
| JP | 2001-509179 | 7/2001 |
| JP | 2003-512407 | 4/2003 |
| WO | WO 90/08799 | 8/1990 |
| WO | WO 98/35630 A2 | 8/1998 |
| WO | WO 98/35630 A3 | 8/1998 |
| WO | WO 98/36729 | 8/1998 |
| WO | WO 98/36729 A1 | 8/1998 |
| WO | WO 98/36729 A2 | 8/1998 |
| WO | WO 99/45890 A1 | 9/1999 |
| WO | WO 01/12679 A1 | 2/2001 |
| WO | WO 01/30307 | 5/2001 |
| WO | WO 01/74301 A1 | 10/2001 |
| WO | WO 01/95862 A1 | 12/2001 |
| WO | WO 02/26197 A2 | 4/2002 |
| WO | WO 02/26197 A3 | 4/2002 |
| WO | WO 02/36039 A1 | 5/2002 |
| WO | WO 02/085313 A1 | 10/2002 |
| WO | WO 02/092021 A1 | 11/2002 |
| WO | WO 03/015720 A1 | 2/2003 |
| WO | WO 03/082142 A1 | 10/2003 |
| WO | WO 2005/007743 A2 | 1/2005 |
| WO | WO 2005/007743 A3 | 1/2005 |
| WO | WO 2005/018476 A2 | 3/2005 |
| WO | WO 2005/018476 A3 | 3/2005 |
| WO | WO 2005/018479 A1 | 3/2005 |
| WO | WO 2005/018484 A2 | 3/2005 |
| WO | WO 2005/018484 A3 | 3/2005 |
| WO | WO 2005/065572 A1 | 7/2005 |
| WO | WO 2006/119003 A1 | 11/2006 |
| WO | WO 2008/033758 A2 | 3/2008 |
| WO | WO 2008/033758 A3 | 3/2008 |
| WO | WO 2008/033893 A1 | 3/2008 |
| WO | WO 2008/033911 A2 | 3/2008 |
| WO | WO 2008/033911 A3 | 3/2008 |

OTHER PUBLICATIONS

Product Instructions for Use, "Kerr Prodigy Condensable," Kerr U.S.A., Orange, CA, 1 pg. (no date available).

Lichkus, J., "Comparative DSC Study of Novel Composite Radica™, Cristobal®+ and Esthet-X®," The IADR/AADR/CADR 85th General Session and Exhibition [online]. New Orleans, LA, Mar. 21-24, 2007 available online [retrieved on Aug. 24, 2007]. Retrieved from the Internet:<URL:http://iadr.confex.com/iadr/2007orleans/techprogram/abstract_90574.htm>; 1 pg.

"REVOTEK™ LC Light-cured Composite Resin for Temporary Resorations" datasheet [online]. GC America Inc., Alsip, IL, [retrieved on Aug. 28, 2007]. Retrieved from the Internet:<URL:http://www.gcamerica.com>; 2 pgs.

U.S. Appl. No. 10/643,748, filed Aug. 19, 2003, Oxman et al.

U.S. Appl. No. 10/643,771, filed Aug. 19, 2003, Kvitrud et al.

U.S. Appl. No. 10/921,648, filed Aug. 19, 2004, Karim et al.

Office Action dated Feb. 23, 2006 for U.S. Appl. No. 10/643,748; 12 pgs.

Office Action dated Jun. 27, 2006 for U.S. Appl. No. 10/643,748; 10 pgs.

Office Action dated Dec. 5, 2006 for U.S. Appl. No. 10/643,748; 8 pgs.

Office Action dated May 11, 2007 for U.S. Appl No. 10/643,748; 10 pgs.

"radica™ provisional & diagnostic resin" datasheet [online]. DENTSPLY Ceramico, Burlington, NJ, [retrieved on Aug. 17, 2007]. Retrieved from the Internet:<URL:http://www.ceramco.com/prod_radica.shtml>; 2 pgs.

U.S. Appl. No. 60/913,037, filed Apr. 20, 2007, Karim.

Japanese Office Action dated Sep. 11, 2008 for Japanese Patent Application No. 2003-520681 (7 pgs).

European Office Action dated Nov. 21, 2008 for European Patent Application No. 02 76 8577.5-2108 (4 pgs).

U.S. Appl. No. 12/250,309, filed Oct. 13, 2008, Karim et al.

Australian Office Action dated Aug. 18, 2006 for Australian Patent Application No. 2002331604 (2 pgs).

Canadian Office Action dated Mar. 26, 2009 for Canadian Patent Application No. 2,454,617 (6 pgs).

Chinese Office Action dated Aug. 26, 2005 for Chinese Patent Application No. 02815839.3 (11 pgs).

Chinese Office Action dated May 12, 2006 for Chinese Patent Application No. 02815839.3 (12 pgs).

* cited by examiner

HARDENABLE SELF-SUPPORTING STRUCTURES AND METHODS

CROSS-REFERENCE TO RELATED APPLICATIONS

This application claims priority to U.S. Provisional Application Ser. No. 60/312,355, filed on Aug. 15, 2001, the entirety of which is incorporated herein by reference.

FIELD OF THE INVENTION

This invention relates to materials, particularly dental materials, and methods of making and using. These materials have sufficient internal strength to be formed into a desired shape that can be maintained during transportation and storage and with sufficient malleability to be subsequently customized into a second shape and then hardened. These materials can be used in a variety of applications, including oral prosthetic devices such as inlays, onlays, veneers, temporary crowns, permanent crowns, bridges, as well as fillings, orthodontic appliances, tooth facsimiles or splints, and dental impression trays.

BACKGROUND

Restorative dentistry is an important market in today's dental industry. In particular, tooth repair with temporary and permanent crowns is a common procedure, typically requiring multiple dental appointments. Current technology uses pastes, two-part powder/liquid systems, preformed metal temporary crowns, and ceramic or porcelain/metal permanent crowns.

Currently available polymerizable resins are typically free radically polymerizable monomers (e.g., acrylates, methacrylates, and acrylamides). These are used together with initiator systems that typically include reducing agents, such as tertiary amines, and oxidizing agents, such as peroxides, as accelerators or activators for free radical polymerization and control of the rate of polymerization.

A typical procedure for making a provisional (i.e., temporary) dental restorative involves the following steps. Initially, an alginate impression is taken before preparing the teeth. The impression is rinsed, set aside, and wrapped in a moist paper towel. The teeth are then prepared and the correct shade of acrylic powder is selected to match the natural teeth. An acrylic liquid resin and the acrylic polymeric powder, one of which includes a reducing agent and the other of which includes an oxidizing agent, are mixed together and placed in the impression. The impression is placed aside until the composition thickens and forms a dull appearance (approximately 45-60 seconds). Meanwhile, the prepared teeth and surrounding tissue are coated with a petroleum jelly, which ensures easy removal of the acrylic temporary from the preparation and protects the teeth and tissue from irritation by the acrylic mixture. The impression with the acrylic mixture is seated in the mouth and held in place for a sufficient time to allow it to harden to a removable state. The acrylic material is removed from the impression and gross excess acrylic is trimmed. The acrylic material is placed in and out of the mouth while the acrylic material is in a rubbery state. The acrylic material is removed from the mouth and set aside until the acrylic is fully cured. The fit of the acrylic restorative is checked and adapted to fit, if necessary. Excess acrylic is trimmed with an acrylic bur or stone and polished to a smooth finish. The acrylic temporary is then cemented into place.

It would be desirable to eliminate the initial mixing of the liquid resin and the polymeric powder and thereby create such prosthetic devices more efficiently. It would also be desirable to eliminate the impression-taking step. Dental waxes, commonly used for taking impressions in the mouth, exhibit many desirable properties for creating devices that are customized to a patient's mouth. These properties include malleability, low memory, sufficient strength to be self-supporting, and the thermal and rheological properties shown in FIG. 1. These wax (e.g., paraffin) materials typically have melting points near 55° C., with softening transitions near 40° C. Elastic and viscous moduli G' and G" are approximately $10^6$ Pascals (Pa) at 25° C., sufficiently low to be easily deformed without being tacky. Although these materials exhibit desirable properties for creating devices customized to fit a patient's mouth, they are not hardenable (e.g., through polymerization), nor do they possess desirable properties such as compressive strength and wear resistance. As a result, these materials are not suitable for dental prosthetic applications.

U.S. Pat. No. 6,057,383 (Völkel et al.) discloses a dental material based on polymerizable waxes, wherein the materials are malleable and curable; however, they are based on little or no filler, typically 0-60% by weight, and high amounts of waxes, typically more than 20% by weight. As such, these materials have generally poor mechanical properties, such as flexural strength and wear resistance. Other thermoplastic molding compounds have been prepared, but these are typically highly viscous above their melting point ($T_m$), and somewhat elastic below $T_m$ due to the high molecular weight of the included polymer. Moreover, these compositions must typically be warmed significantly above room temperature before becoming malleable.

It would be desirable to have highly filled materials that can be preformed into a desirable shape yet be sufficiently malleable, particularly at room temperature or body temperature, to form a custom-shaped device.

SUMMARY

Figure 1:
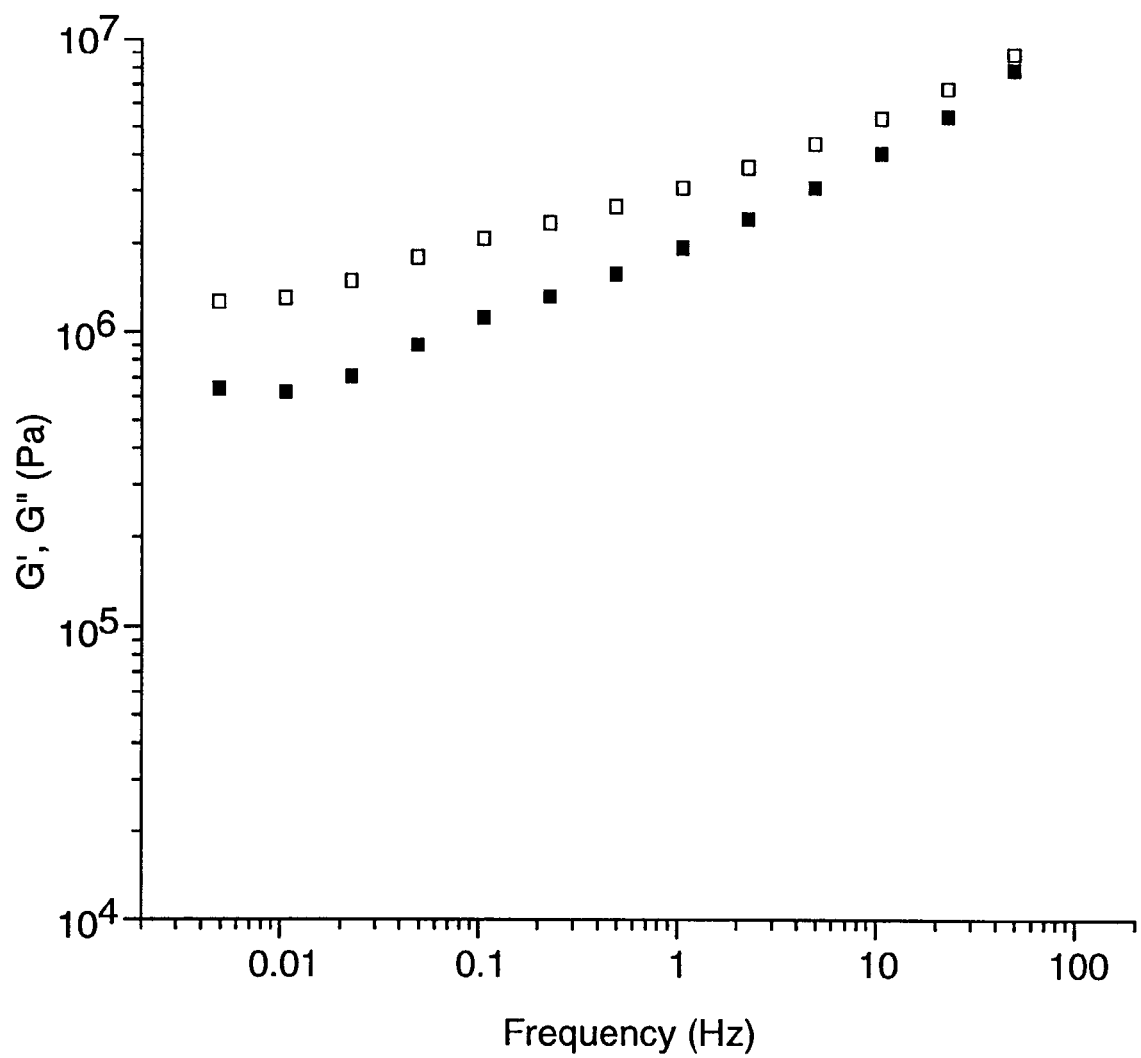
FIG. 1. Rheological response of dental wax (Baseplate Wax All-Season #2 Pink, Patterson Dental Supply, St. Paul, Minn.). Solid symbols represent elastic modulus G', while open symbols represent viscous modulus G".

The present invention provides a composition that includes a resin system, a filler system, and an initiator system. The composition is in the form of a hardenable, self-supporting (i.e., free-standing) structure having a first shape. The self-supporting structure has sufficient malleability to be reformed into a second shape, thereby providing for simplified customization of a device, e.g., simplified customized fitting of a dental prosthetic device. Once reformed into a second shape, the composition can be hardened using, for example, a free radical curing mechanism under standard photopolymerization conditions to form a hardened composition with improved mechanical properties. Significantly, for the compositions of the present invention upon hardening the structure in the second shape, the hardened structure does not need an additional veneering material.

Herein, the "resin system" can include one or more resins, each of which can include one or more monomers, oligomers, and/or polymerizable polymers.

The term "self-supporting" means that the composition is dimensionally stable and will maintain its shape (e.g., preformed shape of a crown) without significant deformation at room temperature (i.e., about 20° C. to about 25° C.) for at least about two weeks when free-standing (i.e., without the support of packaging or a container). Preferably, the compositions of the present invention are dimensionally stable at room temperature for at least about one month, and more preferably, for at least about six months. Preferably, the compositions of the present invention are dimensionally stable at temperatures above room temperature, more preferably up to about 40° C., even more preferably up to about 50° C., and even more preferably up to about 60° C. This definition applies in the absence of conditions that activate the initiator system and in the absence of an external force other than gravity.

The term "sufficient malleability" means that the self-supporting structure is capable of being custom shaped and fitted, for example, to a patient's mouth, under a moderate force (i.e., a force that ranges from light finger pressure to that applied with manual operation of a small hand tool, such as a dental composite instrument).

The unique combination of highly malleable properties (preferably without heating above room temperature or body temperature) before hardening (e.g., cure) and high strength (preferably, a flexural strength of at least about 25 MPa) after hardening provides a composition with numerous potential applications. These applications include, but are not limited to, dental restoratives and dental prostheses, including, but not limited to, temporary, intermediate, and permanent crowns and bridges, inlays, onlays, veneers, implants, dentures, and artificial teeth, as well as dental impression trays, orthodontic appliances (e.g., retainers, night guards), tooth facsimiles or splints, maxillofacial prosthesis, and other customized structures. The compositions of the present invention can also be used as filling materials (particularly packable materials), for example.

A preferred embodiment of the invention is a composition that includes a resin system including a crystalline component, greater than 60 percent by weight (wt-%) of a filler system (preferably, greater than 70 wt-% of a filler system), and an initiator system, wherein the composition is in the form of a hardenable self-supporting structure having a first shape. The self-supporting structure has sufficient malleability to be formed into a second shape, preferably at a temperature of about 15° C. to 38° C. (more preferably, about 20° C. to 38° C., which encompasses typical room temperatures and body temperatures, and most preferably, at room temperature). Advantageously, the compositions of the present invention do not need to be heated above body temperature (or preferably, even about room temperature) to become malleable.

Typically and preferably, at least a portion of the filler system comprises particulate filler. Preferably, in this and various other embodiments, if the filler system includes fibers, the fibers are present in an amount of less than 20 wt-%, based on the total weight of the composition.

The crystalline component provides a morphology that assists in maintaining the self-supporting first shape. This morphology includes a noncovalent structure, which may be a three-dimensional network (continuous or discontinuous) structure. If desired, the crystalline component can include one or more reactive groups to provide sites for polymerizing and/or crosslinking. If such crystalline components are not present or do not include reactive groups, such reactive sites are provided by another resin component, such as an ethylenically unsaturated component.

Thus, for certain embodiments, the resin system preferably includes at least one ethylenically unsaturated component. Preferred ethylenically unsaturated components are selected from the group consisting of mono-, di-, or poly-acrylates and methacrylates, unsaturated amides, vinyl compounds (including vinyl oxy compounds), and combinations thereof. This ethylenically unsaturated component can be the crystalline component, although in certain preferred embodiments it is noncrystalline.

The crystalline component can include polyesters, polyethers, polyolefins, polythioethers, polyarylalkylenes, polysilanes, polyamides, polyurethanes, or combinations thereof. Preferably, the crystalline component includes saturated, linear, aliphatic polyester polyols containing primary hydroxyl end groups. The crystalline component can optionally have a dendritic, hyperbranched, or star-shaped structure, for example.

The crystalline component can optionally be a polymeric material (i.e., a material having two or more repeat units, thereby including oligomeric materials) having crystallizable pendant moieties and the following general formula:

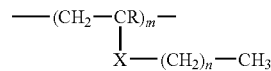

wherein R is hydrogen or a $(C_1-C_4)$alkyl group, X is —$CH_2$—, —C(O)O—, —O—C(O)—, —C(O)—NH—, —HN—C(O)—, —O—, —NH—, —O—C(O)—NH—, —HN—C(O)—O—, —HN—C(O)—NH—, or —$Si(CH_3)_2$—, m is the number of repeating units in the polymer (preferably, 2 or more), and n is great enough to provide sufficient side chain length and conformation to form polymers containing crystalline domains or regions.

Alternative to, or in combination with, the crystalline component, the composition can include a filler that is capable of providing a morphology to the composition that includes a noncovalent structure, which may be a three-dimensional network (continuous or discontinuous) structure, that assists in the maintenance of the first shape. Preferably, such a filler has nanoscopic particles, more preferably, the filler is an inorganic material having nanoscopic particles. To enhance the formation of the noncovalent structure, the inorganic material can include surface hydroxyl groups. Most preferably, the inorganic material includes fumed silica.

Furthermore, the use of one or more surfactants can also enhance the formation of such a noncovalent structure. A particularly preferred composition includes, in addition to a resin system and an initiator system, either a crystalline component, or a filler system that includes a nanoscopic particulate filler (preferably, both a micron-size particulate filler and a nanoscopic particulate filler) and a surfactant system, or both a crystalline component and a filler system and surfactant system. As used herein, a filler system includes one or more fillers and a surfactant system includes one or more surfactants.

Thus, another embodiment of the invention includes a composition that includes a resin system, a filler system at least a portion of which is an inorganic material having nanoscopic particles with an average primary particle size of no greater than about 50 nanometers (nm), a surfactant system, and an initiator system. The composition is in the form of a hardenable self-supporting structure having a first shape and sufficient malleability to be formed into a second shape, preferably at a temperature of about 15° C. to 38° C. In such preferred embodiments with a surfactant system and nanoscopic particles, the resin system preferably includes at least one ethylenically unsaturated component, and the filler system is present in an amount of greater than 50 wt-%.

In a preferred embodiment, a composition of the present invention includes a resin system that includes: a noncrystalline component selected from the group consisting of mono-, di-, or poly-acrylates and methacrylates, unsaturated amides, vinyl compounds, and combinations thereof; and a crystalline component selected from the group consisting of polyesters, polyethers, polyolefins, polythioethers, polyarylalkylenes, polysilanes, polyamides, polyurethanes, polymeric materials (including oligomeric materials) having crystallizable pendant moieties and the following general formula:

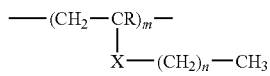

wherein R is hydrogen or a $(C_1-C_4)$alkyl group, X is —$CH_2$—, —C(O)O—, —O—C(O)—, —C(O)—NH—, —HN—C(O)—, —O—, —NH—, or —O—C(O)—NH—, —HN—C(O)—O—, —HN—C(O)—NH—, or —$Si(CH_3)_2$—, m is the number of repeating units in the polymer (preferably, 2 or more), and n is great enough to provide sufficient side chain length and conformation to form polymers containing crystalline domains or regions, and combinations thereof. The composition further includes greater than about 60 wt-% of a filler system and an initiator system, wherein the composition is in the form of a hardenable self-supporting structure having a first shape. The self-supporting structure has sufficient malleability to be formed into a second shape at a temperature of about 15° C. to 38° C. Preferably, if the filler system includes fibers, the fibers are present in an amount of less than 20 wt-%, based on the total weight of the composition.

In yet another preferred embodiment, a composition of the present invention includes a resin system comprising a crystalline compound of the formula:

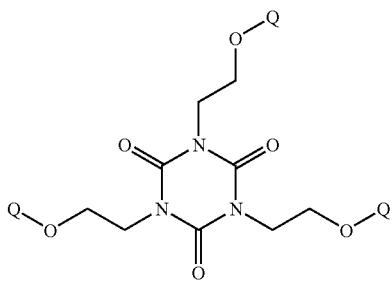

wherein each Q independently comprises polyester segments, polyamide segments, polyurethane segments, polyether segments, or combinations thereof; a filler system; and an initiator system; wherein the composition is in the form of a hardenable self-supporting structure having a first shape and sufficient malleability to be formed into a second shape.

The compositions of the present invention can be in the form of a variety of dental products, which can be in rope form (as for filling materials), globular form, sheet form, or in the form of a preformed article, which is in a complex or semi-finished shape (as that of a preformed crown). Typically, the dental products referred to herein are in a hardenable form, but the term can also be used for the final dental product in its hardened form.

Preferred dental products include a preformed crown, a preformed inlay, a preformed onlay, a preformed bridge, a preformed veneer, a preformed orthodontic appliance, a preformed maxillofacial prosthesis, a preformed tooth facsimile, or a preformed tooth splint. Alternatively, the dental product can be a filling material (such as a packable material). Particularly preferred dental products include a preformed crown and a preformed bridge, and more preferably, a preformed crown.

In one preferred embodiment, the present invention provides a preformed dental crown that includes a composition including a resin system, a filler system, and an initiator system, wherein the composition is in the form of a hardenable self-supporting structure having a first shape and sufficient malleability to be formed into a second shape.

The present invention also provides a dental impression tray. A preferred tray includes a resin system, a filler system, and an initiator system in the form of a hardenable self-supporting structure having a first shape and sufficient malleability to be formed into a second shape at a temperature of about 15° C. to 38° C. Preferably, the dental impression tray includes at least one structured surface. Preferably, the structured surface is formed by a porous substrate. Alternatively, the structured surface is a microreplicated surface.

The present invention also provides a method of preparing a composition. The method includes combining a resin system, a filler system, and an initiator system to form a mixture; and forming the mixture into a hardenable self-supporting structure having a first shape; wherein the hardenable self-supporting structure having a first shape has sufficient malleability to be formed into a second shape.

The present invention also provides a method of preparing a dental product. The method includes: providing a composition comprising a resin system, a filler system, and an initiator system, wherein the composition is in the form of a hardenable, self-supporting, malleable structure having a first semi-finished shape (e.g., that of a preformed crown or preformed bridge); forming the self-supporting, malleable structure into a second shape; and hardening the self-supporting structure having the second shape to form a dental product. Preferably, forming the self-supporting, malleable structure into a second shape occurs at a temperature of about 15° C. to 38° C. Herein, forming the self-supporting, malleable structure into a second shape occurs under a force that ranges from light finger pressure to that applied with manual operation of a small hand tool, such as a dental composite instrument.

The present invention also provides a method of preparing a dental tray. The method includes: providing a composition comprising a resin system, a filler system, and an initiator system, wherein the composition is in the form of a hardenable, self-supporting, malleable structure having a first semi-finished shape of a preformed dental tray; forming the self-supporting, malleable structure into a second shape custom fit to the patient; and hardening the self-supporting structure having the second shape to form a dental tray. Preferably, forming the self-supporting, malleable structure into a second shape occurs a temperature of about 15° C. to 38° C.

The present invention also provides a compound of the formula:

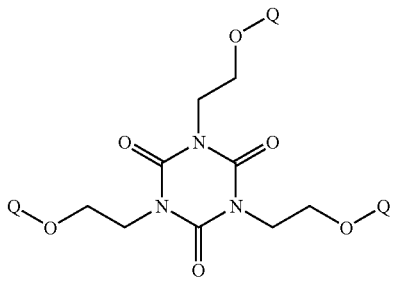

wherein each Q independently comprises polyester segments, polyamide segments, polyurethane segments, polyether segments, or combinations thereof.

DETAILED DESCRIPTION OF PREFERRED EMBODIMENTS OF THE INVENTION

The present invention provides a composition that includes a resin system, a filler system, and an initiator system in the form of a hardenable self-supporting (i.e., free-standing) structure having a first shape, preferably the shape of a dental crown. The resin system (one or more resins), filler system (one or more fillers), and initiator system (one or more initiators) are chosen such that: the composition can be relatively easily molded to form the initial self-supporting structure; the self-supporting structure maintains its first shape at room temperature for at least about two weeks (in the absence of conditions that activate the initiator system and in the absence of an external force other than gravity), and the self-supporting structure has sufficient malleability to be reformed into a second shape (preferably at a temperature of about 15° C. to 38° C., more preferably, at a temperature of about 20° C. to 38° C., and most preferably, at room temperature).

The compositions of the present invention are particularly well suited for preformed dental products. As used herein, a preformed dental product is one that is provided to the dentist in the desired semi-finished shape (a first shape), which can then be modified (e.g., molded, adapted, trimmed) for fit in a patient (a second shape). Herein, a semi-finished shape of a preformed article is the facsimile of what the final shaped article is to be, and is not the shape of a rope, globule, or sheet. This is described in greater detail below. Typically, this means that the compositions of the present invention have been formed into a shape, preferably using a mold with a positive and negative impression, and the resultant shaped material released from the shaping device, preferably a mold, without significant deformation.

Although the compositions of the present invention are particularly useful for preformed crowns and other preformed dental products having a complex shape, they can be used as materials for preparing fillings, etc. The requirements for the latter are less stringent when it comes to molding, removal from a mold, packaging, transportation, and the like, than is required for preformed crowns or other preformed dental articles of a complex shape, typically because filling materials are provided to the dentist in a rope form.

Generally, hardenable self-supporting compositions of the present invention have rheological properties similar to waxes below the waxes' melting points in that they can be relatively easily deformed (i.e., they are malleable) and exhibit low elastic recovery. However, the compositions of the present invention are not free-flowing fluids (i.e., liquids) above their softening points. That is, the compositions of the present invention display appreciable mass flow under moderate (e.g., hand) pressure, but not liquid flow above their softening points.

Typically, elastic and viscous dynamic moduli of hardenable compositions of the present invention vary over a wide range. Furthermore, the hardenable compositions are typically largely free from tack. Preferably, the elastic dynamic modulus (i.e., elastic modulus) G' is at least about 100 kilopascals (kPa), more preferably, at least about 200 kPa, and most preferably, at least about 1000 kPa, at a frequency of about 0.005 Hz. Preferably, the elastic modulus G' is no greater than about 50,000 kPa, more preferably, no greater than about 10,000 kPa, and most preferably, no greater than about 5000 kPa, at a frequency of about 0.005 Hz. Preferably, the viscous dynamic modulus (i.e., viscous modulus) G" is at least about 50 kPa, more preferably, at least about 200 kPa, and most preferably, at least about 1000 kPa, at a frequency of about 0.005 Hz. Preferably, the viscous modulus G" is no greater than about 50,000 kPa, more preferably, no greater than about 10,000 kPa, and most preferably, no greater than about 5000 kPa, at a frequency of about 0.005 Hz.

The desired self-supporting (i.e., free-standing) structure of hardenable compositions of the present invention can be maintained by creating a morphology that includes a noncovalent structure, which may be a three-dimensional network (continuous or discontinuous) structure. This can result from the use of a crystalline component in the resin system, or the use of one or more fillers, typically aided by one or more surfactants, or the use of both a crystalline component and one or more fillers optionally combined with one or more surfactants. These components are discussed in more detail below.

With the appropriate initiator system, e.g., a free radical photoinitiator, hardenable compositions of the present invention can be hardened (e.g., cured) to form the desired product. Preferably, the resultant hardened composition (i.e., the hardened structure) has a flexural strength of at least about 25 megapascals (MPa), more preferably, at least about 40 MPa, even more preferably, at least about 50 MPa, and most preferably, at least about 60 MPa.

For certain applications (e.g., crowns), the resultant hardened composition is an enamel-like solid, preferably having a compressive strength of at least about 100 MPa. For other applications, such as dental impression trays, materials with lower compressive strengths can be used.

For certain applications (e.g., crowns), the resultant hardened composition is an enamel-like solid, preferably having a diametral tensile strength of at least about 20 MPa. For other applications, such as dental impression trays, materials with lower diametral tensile strengths can be used.

For certain applications (e.g., crowns), the resultant hardened composition is an enamel-like solid, preferably having a flexural modulus of at least about 1000 MPa. For other applications, such as dental impression trays, materials with lower flexural modulus can be used.

Resin System

Hardenable compositions of the present invention include a resin system. The resin system includes one or more hardenable organic resins capable of forming a hardened material having sufficient strength and hydrolytic stability to render them suitable for use in the oral environment.

As used herein, a resin includes one or more monomers, oligomers, and/or polymerizable polymers, including combinations thereof. Although, in this context oligomers and polymers are both used, the terms "polymer" and "polymeric" are used herein to refer to any materials having 2 or more repeat units, thereby encompassing oligomers. Thus, unless otherwise specified, polymers include oligomers. Furthermore, the term polymer is used herein to encompass both homopolymers and copolymers, and the term copolymer is used herein to encompass materials with two or more different repeat units (e.g., copolymers, terpolymers, tetrapolymers).

A preferred organic resin is hardenable (e.g., polymerizable and/or crosslinkable), preferably by a free radical mechanism, and includes monomers, oligomers, and/or polymers. The resin system includes a reactive component (i.e., a component capable of polymerizing and/or crosslinking), which may or may not be crystalline. Resin systems that include noncrystalline reactive components may optionally include a crystalline component, which may or may not be reactive.

Preferably, at least some of the resin components include ethylenic unsaturation and are capable of undergoing addition polymerization. A suitable resin preferably includes at least one ethylenically unsaturated monomer (i.e., includes at least one carbon-carbon double bond).

Examples of suitable polymerizable resin components include: mono-, di-, or poly-(meth)acrylates (including acrylates and methacrylates) such as methyl acrylate, methyl methacrylate, ethyl acrylate, isopropyl methacrylate, n-hexyl acrylate, stearyl acrylate, allyl acrylate, glycerol mono- and diacrylate, glycerol triacrylate, ethyleneglycol diacrylate, diethyleneglycol diacrylate, triethyleneglycol dimethacrylate, 1,3-propanediol diacrylate, 1,3-propanediol dimethacrylate, trimethylolpropane triacrylate, 1,2,4-butanetriol trimethacrylate, 1,4-cyclohexanediol diacrylate, pentaerythritol triacrylate, pentaerythritol tetraacrylate, pentaerythritol tetramethacrylate, sorbitol hexacrylate, bis(1-(2-acryloxy))-p-ethoxyphenyldimethylmethane, bis(1-(3-acryloxy-2-hydroxy))-p-propoxyphenyldimethylmethane, tris(hydroxyethylisocyanurate) trimethacrylate, 2-hydroxyethyl methacrylate, 2-hydroxypropyl methacrylate, tetrahydrofurfuryl methacrylate, ethylene glycol dimetliacrylate, triethylene glycol dimethacrylate, bisGMA, ethoxylated bisphenolA diacrylate, ethoxylated bisphenolA dimethacrylate, polyethylene glycol dimethacrylate, the bisacrylates and bis-methacrylates of polyethylene glycols of molecular weight 200-500, copolymerizable mixtures of acrylated monomers such as those of U.S. Pat. No. 4,652,274 (Boettcher et al.), and acrylated oligomers such as those of U.S. Pat. No. 4,642,126 (Zador et al.); unsaturated amides such as (meth)acrylamides (i.e., acrylamides and methacrylamides), methylene bis-acrylamide, methylene bis-methacrylamide, 1,6-hexamethylene bis-acrylamide, diethylene triamine trisacrylamide, and beta-methacrylamidoethyl methacrylate, diacetone acrylamide, and diacetone methacrylamide; urethane (meth)acrylates; and vinyl compounds such as styrene, diallyl phthalate, divinyl succinate, divinyl adipate, and divinylphthalate. Mixtures of two or more such materials can be used if desired in the resin system.

Preferably, the total amount of the resin system is at least about 10 wt-%, more preferably, at least about 13 wt-%, and most preferably, at least about 15 wt-%, based on the total weight of the composition. Preferably, the total amount of the resin system is no greater than about 60 wt-%, more preferably, no greater than about 50 wt-%, and most preferably, no greater than about 40 wt-%, based on the total weight of the composition.

The above-listed components are typically noncrystalline (i.e., amorphous). The resin system can also include a crystalline component to impart the noncovalent three-dimensional structure for maintaining the initial preformed shape. This crystalline component may or may not have a reactive group capable of polymerizing (also including crosslinking). Preferably, the crystalline component is polymerizable. Preferably, the crystalline component is polymeric (including oligomeric). More preferably, the crystalline component is a polymerizable polymeric material.

By "crystalline" it is meant that the material displays a crystalline melting point at 20° C. or above when measured in the composition by differential scanning calorimetry (DSC). The peak temperature of the observed endotherm is taken as the crystalline melting point. The crystalline phase includes multiple lattices in which the material assumes a conformation in which there is a highly ordered registry in adjacent chemical moieties of which the material is constructed. The packing arrangement (short order orientation) within the lattice is highly regular in both its chemical and geometric aspects.

A crystalline component may be in a "semicrystalline state" in that long segments of polymer chains appear in both amorphous and crystalline states or phases at 20° C. or above. The amorphous phase is considered to be a randomly tangled mass of polymer chains. The X-ray diffraction pattern of an amorphous polymer is a diffuse halo indicative of no ordering of the polymer structure. Amorphous polymers show softening behavior at the glass transition temperature, but no true melt or first order transition. A material in a semicrystalline state shows characteristic melting points, above which the crystalline lattices become disordered and rapidly lose their identity. The X-ray diffraction pattern of such "semicrystalline" materials generally is distinguished by either concentric rings or a symmetrical array of spots, which are indicative of the nature of the crystalline order. Thus, herein a "crystalline" component encompasses semicrystalline materials.

The crystalline component includes at least one material that crystallizes, preferably above room temperature (i.e., 20° C. to 25° C.). Such crystallinity, that may be provided by the aggregation of crystallizable moieties present in the component (e.g., when the component is a polymer, in the backbone (i.e., main chain) or pendant substituents (i.e., side chains) of the component), can be determined by well known crystallographic, calorimetric, or dynamic/mechanical methods. For the purposes of the present invention, this component imparts to the resin system at least one melting temperature ($T_m$) as measured experimentally (for example by DSC) of greater than about 20° C. Preferably, this component imparts a $T_m$ to the resin system of about 30° C.-100° C. If more than one crystalline material is used in the crystalline component, more than one distinct melting point may be seen.

The number average molecular weight of the crystalline component may vary over a broad range. Preferably, the molecular weight is less than 10,000 grams per mole (g/mol), and preferably no greater than about 5000 g/mol. Preferably, the molecular weight is at least about 150 g/mol, and more preferably at least about 400 g/mol. At molecular weights less than about 150 the crystalline melting point may be too low. At molecular weights greater than about 10,000 the crystalline melting point may be too high.

The crystalline monomers suitable for use in the resin system include monomers containing urethane, ether, ester, amide, imide groups, or combinations thereof. Preferred crystalline monomers contain reactive groups capable of polymerizing and/or crosslinking. Especially preferred are monomers with a reactive functionality greater than one.

The crystalline polymers (including oligomers) suitable for use in the resin system can have crystalline main chain (i.e., linear) or pendant (i.e., side chain) segments. Preferred materials also contain reactive groups capable of polymerizing and/or crosslinking. Especially preferred are crystalline oligomers or prepolymers with a reactive functionality of at least two.

Examples of suitable crystalline materials having crystallizable main chain or backbone segments include, but are not limited to, polyesters (including polycaprolactones), polyethers, polythioethers, polyarylalkylenes, polysilanes, polyamides, polyolefins (preferably, formed from lower, e.g., $C_2$-$C_3$, olefins), and polyurethanes.

Preferred crystalline materials are saturated, linear, aliphatic polyester polyols (particularly diols) containing primary hydroxyl end groups. Examples of commercially available materials useful as the crystalline component in the resin systems of the invention include some resins available under the trade designation LEXOREZ from Inolex Chemical Co., Philadelphia, Pa. Examples of other polyester polyols useful in the compositions of the invention are those available under the trade designation RUCOFLEX from Ruco Polymer Corp., Hicksville, N.Y. Examples of polycaprolactones that are useful in the invention include those available under the trade designations TONE 0230, TONE 0240, and TONE 0260 from Dow Chemical Co., Midland, Mich. Especially preferred materials are saturated, linear, aliphatic polyester polyols that are modified (e.g., through primary hydroxyl end groups) to introduce polymerizable, unsaturated functional groups, e.g., polycaprolactone diol reacted with 2-isocyanatoethyl methacrylate, methacryloyl chloride, or methacrylic anhydride.

The crystalline materials may also have a dendritic, hyperbranched, or star-shaped structure, for example, with varying degrees of branching. Dendritic polymers are polyfunctional compounds and include any of the known dendritic architectures including dendrimers, regular dendrons, dendrigrafts, and hyperbranched polymers. Dendritic polymers are polymers with densely branched structures having a large number of end reactive groups. A dendritic polymer includes several layers or generations of repeating units which all contain one or more branch points. Dendritic polymers, including dendrimers and hyperbranched polymers, can be prepared by condensation, addition, or ionic reactions of monomeric units having at least two different types of reactive groups.

Dendritic polymers are comprised of a plurality of dendrons that emanate from a common core, which core usually comprises a group of atoms. Dendritic polymers generally consist of peripheral surface groups, interior branch junctures having branching functionalities greater than or equal to two, and divalent connectors that covalently connect neighboring branching junctures.

Dendrons and dendrimers may be ideal or non-ideal, i.e., imperfect or defective. Imperfections are normally a consequence of either incomplete chemical reactions or unavoidable competing side reactions.

Hyperbranched polymers are dendritic polymers that contain high levels of non-ideal irregular branching arrays as compared with the more nearly perfect regular structure dendrimers. Specifically, hyperbranched polymers contain a relatively high number of irregular branching arrays in which not every repeat unit contains a branch juncture. Consequently, hyperbranched polymers may be viewed as intermediate between linear polymers and dendrimers. Yet they are dendritic because of their relatively high branch-juncture content per individual macromolecule.

Star-shaped polymers typically consist of polymer chains emanating from a central core.

The preparation and characterization of dendrimers, dendrons, dendrigrafts, hyperbranched polymers, and star-shaped are well known. Examples of dendrimers and dendrons, and methods of synthesizing the same are set forth in U.S. Pat. Nos. 4,507,466 (Tomalia et al.), 4,558,120 (Tomalia et al.), 4,568,737 (Tomalia et al.), 4,587,329 (Tomalia et al.), 4,631,337 (Tomalia et al.), 4,694,064 (Tomalia et al.), 4,713,975 (Tomalia et al.), 4,737,550 (Tomalia ), 4,871,779 (Killat et al.), and 4,857,599 (Tomalia et al.). Examples of hyperbranched polymers and methods of preparing the same are set forth, for example, in U.S. Pat. No. 5,418,301 (Hult et al.). Some dendritic polymers are also commercially available. For example, 3- and 5-generation hyperbranched polyester polyols may be obtained from Perstorp Polyols, Inc., Toledo, Ohio. Examples of star polymers and methods of preparing the same are set forth, for example, in U.S. Pat. Nos. 5,830,986 (Merrill, et al.), 5,859,148 (Borggreve, et al.), 5,919,870 (Letchford, et al.), and 6,252,014 (Knauss).

The dendritic polymers useful in this invention may include any number of generations, preferably three to five generations.

Generally, any of the known dendritic polymers having crystalline peripheral groups, or having peripheral groups that can be reacted with another compound to crystalline peripheral groups are suitable for use in the resin system in the compositions of this invention. Examples of suitable dendritic polymers include polyethers, polyesters, polythioether, polyarylalkylenes, polysilanes, polyamides, polyurethanes, and any other condensation polymers.

Examples of suitable crystalline polymeric materials having crystallizable pendant moieties (i.e., side chains) include, but are not limited to polymeric materials having the following general formula:

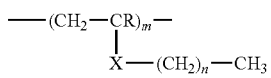

wherein R is hydrogen or a ($C_1$-$C_4$)alkyl group, X is —$CH_2$—, —C(O)O—, —O—C(O)—, —C(O)—NH—, —HN—C(O)—, —O—, —NH—, —O—C(O)—NH—, —HN—C(O)—O—, —HN—C(O)—NH—, or —Si(CH_3)_2—, m is the number of repeating units in the polymer, and n is great enough to provide sufficient side chain length and conformation to form polymers containing crystalline domains or regions. Preferably, m is at least 2, and more preferably, 2 to 100, and preferably, n is at least 10. The crystalline polymeric materials may be prepared by the polymerization of monomers containing the pendant (side chain) crystallizable moieties or by the introduction of pendant crystallizable moieties by chemical modification of a polyacrylate, polymethacrylate, polyacrylamide, polymethacrylamide, polyvinyl ester, or poly-α-olefin polymers or copolymers. The preparation and morphology/conformational properties that determine the crystalline character of such side chain crystallizable or "comb-like" polymers are reviewed by Plate and Shibaev, "Comb-Like Polymers. Structure and Properties," *Journal of Polymer Science, Macromolecular Reviews*, 8, 117-253 (1974).

Examples of suitable crystalline materials are acrylate or methacrylate polymers derived from acrylate or methacrylate esters of nontertiary higher alkyl alcohols. As used herein, the term "(meth)acrylate" means methacrylate or acrylate. The alkyl groups of these alcohols contain at least about 12, preferably about 16-26, carbon atoms. Examples of crystalline monomers that can be used to make crystalline polymeric materials include dodecyl (meth)acrylate, isotridecyl (meth)acrylate, n-tetradecyl (meth)acrylate, n-hexadecyl (meth)acrylate, n-octadecyl (meth)acrylate, behenyl (meth)acrylate, eicosanyl (meth)acrylate, and mixtures thereof. Hexadecyl (methacrylates) and octadecyl (meth)acrylates are commercially available from Monomer-Polymer & Dajac Laboratories, Inc., Feasterville, Pa., and Polysciences, Inc., Warrington, Pa. (Meth)acrylate esters of non-tertiary alcohols, the alkyl portions of which comprise from about 30 to about 50 carbon atoms, are commercially available under the trade designation UNILIN from Petrolite Corp., Tulsa, Okla. As long as the crystalline oligomer or polymer has a melting point, it can include noncrystallizable monomers. Acrylate or methacrylate or other vinyl monomers that are free-radically reactive may optionally be utilized in conjunction with one or more of the side chain crystallizable acrylate and methacrylate monomers provided that the resultant polymer has a melting or softening temperature above room temperature. Examples of such free-radically reactive monomers include, but are not limited to, tert-butyl acrylate, isobornyl acrylate, butyl methacrylate, vinyl acetate, acrylonitrile, styrene, isooctyl acrylate, n-butyl acrylate, 2-ethylhexyl acrylate, and the like. Various combinations of these monomers can be used.

Also suitable are side chain crystalline polymeric materials derived from higher α-olefin monomers, such as poly-1-decene, poly-1-dodecene, poly-1-tetradecene, and poly-1-hexadecene, and higher vinyl esters, such as vinyl tetradecanoate, vinyl hexadecanoate and vinyl octadecanoate.

Additional side chain crystalline polymeric materials for use in the present invention include polymers with pendant polymerizable groups. The pendant polymerizable groups may be introduced by the incorporation of functional monomers in the side chain crystalline polymer.

Useful functional monomers include those unsaturated aliphatic, cycloaliphatic, and aromatic compounds having up to about 36 carbon atoms that include a functional group capable of further reaction, such as a hydroxyl, amino, azlactone, oxazolinyl, 3-oxobutanoyl (i.e., acetoacetyl), carboxyl, isocyanato, epoxy, aziridinyl, acyl halide, vinyloxy, or anhydride group.

Also suitable are functional monomers having the general formula

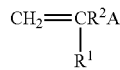

wherein $R^1$ is hydrogen, a ($C_1$ to $C_4$)alkyl group, or a phenyl group, preferably hydrogen or a methyl group; $R^2$ is a single bond or a divalent linking group that joins an ethylenically unsaturated group to functional group A and preferably contains up to 34, more preferably up to 18, most preferably up to 10 carbon atoms, and, optionally, oxygen and nitrogen atoms and, when $R^2$ is not a single bond, is preferably selected from

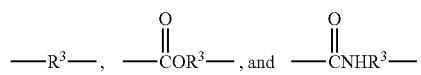

in which $R^3$ is an alkylene group having 1 to 6 carbon atoms, a 5- or 6-membered cycloalkylene group having 5 to 10 carbon atoms, or an alkylene-oxyalkylene in which each alkylene includes 1 to 6 carbon atoms or is a divalent aromatic group having 6 to 16 carbon atoms; and A is a functional group, capable of reaction with a co-reactive functional group (which is part of an unsaturated monomer) to form a covalent bond, preferably selected from the class consisting of hydroxyl, amino (especially secondary amino), carboxyl, isocyanato, aziridinyl, epoxy, acyl halide, vinyloxy, azlactone, oxazolinyl, acetoacetyl, and anhydride groups.

Representative hydroxyl group-substituted functional monomers include the hydroxyalkyl (meth)acrylates and hydroxyalkyl (meth)acrylamides such as 2-hydroxyethyl (meth)acrylate, 2-hydroxypropyl (meth)acrylate, 3-chloro-2-hydroxypropylmethyl (meth)acrylate, 2-hydroxyethyl (meth)acrylamide, 4-hydroxycyclohexyl (meth)acrylate, 3-acryloyloxyphenol, 2-(4-acryloyloxyphenyl)-2-(4-hydroxyphenyl)propane (also called bisphenol A monoacrylate), 2-propyn-1-ol, and 3-butyn-1-ol.

Representative amino group-substituted functional monomers include 2-methyl aminoethyl methacrylate, 3-aminopropyl methacrylate, 4-aminocyclohexyl methacrylate, N-(3-aminophenyl)acrylamide, 4-aminostyrene, N-acryloylethylenediamine, and 4-aminophenyl-4-acrylamidophenylsulfone.

Representative azlactone group-substituted functional monomers include 2-ethenyl-1,3-oxazolin-5-one; 2-ethenyl-4-methyl-1,3-oxazolin-5-one; 2-isopropenyl-1,3-oxazolin-5-one; 2-isopropenyl-4-methyl-1,3-oxazolin-5-one; 2-ethenyl-4,4-dimethyl-1,3-oxazolin-5-one; 2-isopropenyl-4,4-dimethyl-1,3-oxazolin-5-one; 2-ethenyl-4-methyl-4-ethyl-1,3-oxazolin-5-one; 2-isopropenyl-3-oxa-1-aza[4.5]spirodec-1-ene-4-one; 2-ethenyl-5,6-dihydro-4$\underline{H}$-1,3-oxazin-6-one; 2-ethenyl-4,5,6,7-tetrahydro-1,3-oxazepin-7-one; 2-isopropenyl-5,6-dihydro-5,5-di(2-methylphenyl)-4 $\underline{H}$-1,3-oxazin-6-one; 2-acryloyloxy-1,3-oxazolin-5-one; 2-(2-acryloyloxy)ethyl-4,4-dimethyl-1,3-oxazolin-5-one; 2-ethenyl-4,5-dihydro-6$\underline{H}$-1,3-oxazin-6-one, and 2-ethenyl-4,5-dihydro-4,4-dimethyl-6$\underline{H}$-1,3-oxazin-6-one.

Representative oxazolinyl group-substituted functional monomers include 2-vinyl-2-oxazoline, 2-isopropenyl-2-oxazoline, 2-(5-hexenyl)-2-oxazoline, 2-acryloxy-2-oxazoline, 2-(4-acryloxyphenyl)-2-oxazoline, and 2-methacryloxy-2-oxazoline.

Representative acetoacetyl group-substituted functional monomers include 2-(acetoacetoxy)ethyl (meth)acrylate, styryl acetoacetate, isopropenyl acetoacetate, and hex-5-enyl acetoacetate.

Representative carboxyl group-substituted functional monomers include (meth)acrylic acid, 3-(meth)acryloyloxy-propionic acid, 4-(meth)acryloyloxy-butyric acid, 2-(meth)acryloyloxy-benzoic acid, 3-(meth)acryloyloxy-5-methyl benzoic acid, 4-(meth)acryloyloxymethyl-benzoic acid, phthalic acid mono-(2-(meth)acryloyloxy-ethyl) ester, 2-butynoic acid, and 4-pentynoic acid.

Representative isocyanate group-substituted functional monomers include 2-isocyanatoethyl (meth)acrylate, 3-isopropenyl dimethy benzyl isocyanate, 3-isocyanatopropyl (meth)acrylate, 4-isocyanatocyclohexyl (meth)acrylate, 4-isocyanatostyrene, 2-methyl-2-propenoyl isocyanate, 4-(2-acryloyloxyethoxycarbonylamino)phenylisocyanate, allyl 2-isocyanatoethylether, and 3-isocyanato-1-propene.

Representative epoxy group-substituted functional monomers include glycidyl (meth)acrylate, thioglycidyl (meth)acrylate, 3-(2,3-epoxypropxy)phenyl (meth)acrylate, 2-[4-(2,3-epoxypropoxy)phenyl]-2-(4-acryloyloxy-phenyl) propane, 4-(2,3-epoxypropoxy)cyclohexyl (meth)acrylate, 2,3-epoxycyclohexyl (meth)acrylate, and 3,4-epoxycyclohexyl (meth)acrylate.

Representative aziridinyl group-substituted functional monomers include N-(meth)acryloylaziridine, 2-(1-aziridinyl)ethyl (meth)acrylate, 4-(1-aziridinyl)butyl (meth)acrylate, 2-(2-(1-aziridinyl)ethoxy)ethyl (meth)acrylate, 2-(2-(1-aziridinyl)ethoxycarbonylamino)ethyl (meth)acrylate, 12-(2-(2,2,3,3-tetramethyl-1-aziridinyl)ethoxycarbonylamino) dodecyl (meth)acrylate, and 1-(2-propenyl)aziridine.

Representative acyl halide group-substituted functional monomers include (meth)acryloyl chloride, α-chloroacryloyl chloride, acryloyloxyacetyl chloride, 5-hexenoyl chloride, 2-(acryloyloxy) propionyl chloride, 3-(acryloylthioxy) propionoyl chloride, and 3-(N-acryloyl-N-methylamino) propionoyl chloride.

Representative vinyloxy group-substituted functional monomers include 2-(ethenyloxy)ethyl (meth)acrylate, 3-(ethynyloxy)-1-propene, 4-(ethynyloxy)-1-butene, and 4-(ethenyloxy)butyl-2-acrylamido-2,2-dimethylacetate.

Representative anhydride group-substituted functional monomers include maleic anhydride, acrylic anhydride, itaconic anhydride, 3-acryloyloxyphthalic anhydride, and 2-methacryloxycyclohexanedicarboxylic acid anhydride.

Starting from the functional main chain (i.e., linear) or pendant (i.e., side chain) crystalline oligomers or polymer segments, the introduction of polymerizable groups preferably takes place by reaction with suitable unsaturated compounds, in particular (meth)acrylic, allyl, or vinyl compounds, according to known methods of organic chemistry. Polymerizable methacrylate groups can be introduced, for example, by esterification of alcohol groups on the polymer with methacrylic acid or by acylation with methacrylic acid chloride or methacrylic acid anhydride. Furthermore, the reaction of alcohol groups on the crystalline polymer with 2-isocyanatoethyl methacrylate (IEM) is particularly suitable.

Analogously, the functionalized crystalline starting materials can be modified with other unsaturated polymerizable groups, such as acrylic, vinyl, allyl, vinyl ether, or styryl in place of methacrylic groups. Suitable reagents are acrylic acid, acrylic acid chloride, vinyl acetic acid, and 4-vinyl benzoic acid. Preferred polymerizable groups are methacrylate and acrylate groups.

Another crystalline component includes compounds of the formula:

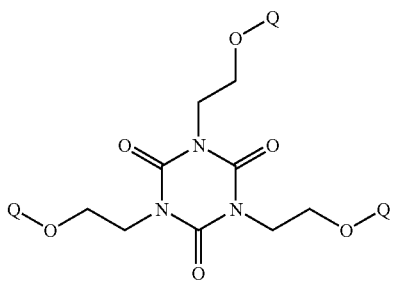

wherein each Q independently includes polyester segments, polyamide segments, polyurethane segments, polyether segments, or combinations thereof. Preferably, each Q independently includes poly(caprolactone) segments. More preferably, such crystalline compounds include polymerizable groups, such as epoxy, acid, alcohol, and ethylenically unsaturated reactive sites. Particularly preferred such materials include unsaturated polymerizable groups, such as methacrylic, acrylic, vinyl, and styryl groups.

Filler System

Fillers for use in the filler system may be selected from a wide variety of conventional fillers for incorporation into resin systems. Preferably, the filler system includes one or more conventional materials suitable for incorporation in compositions used for medical applications, for example, fillers currently used in dental restorative compositions. Thus, the filler systems used in the compositions of the present invention are incorporated into the resin systems, and particularly mixed with the crystalline component of the resin system.

Fillers may be either particulate or fibrous in nature. Particulate fillers may generally be defined as having a length to width ratio, or aspect ratio, of 20:1 or less, and more commonly 10:1 or less. Fibers can be defined as having aspect ratios greater than 20:1, or more commonly greater than 100:1. The shape of the particles can vary, ranging from spherical to ellipsoidal, or more planar such as flakes or discs. The macroscopic properties can be highly dependent on the shape of the filler particles, in particular the uniformity of the shape.

Preferred particulate filler is finely divided and has an average particle size (preferably, diameter) of less than about 10 micrometers (i.e., microns). Preferred micron-size particulate filler has an average particle size of at least about 0.2 microns up to 1 micrometers. Nanoscopic particles have an average primary particle size of less than 200 nm (0.2 microns). The filler can have a unimodal or polymodal (e.g., bimodal) particle size distribution.

Micron-size particles are very effective for improving post-cure wear properties. In contrast, nanoscopic fillers are commonly used as viscosity and thixotropy modifiers. Due to their small size, high surface area, and associated hydrogen bonding, these materials are known to assemble into aggregated networks. Materials of this type ("nanoscopic" materials) have average primary particle sizes (i.e., the largest dimension, e.g., diameter, of unaggregated material) of less than 200 nanometers (nm). Preferably, the nanoscopic particulate material has an average primary particle size of at least 2 nanometers (nm), and preferably at least about 7 nm. Preferably, the nanoscopic particulate material has an average primary particle size of no greater than about 50 nm, and more preferably no greater than about 20 nm in size. The average surface area of such a filler is preferably at least about 20 square meters per gram ($m^2/g$), more preferably, at least about 50 $m^2/g$, and most preferably, at least about 100 $m^2/g$.

The filler can be an inorganic material. It can also be a crosslinked organic material that is insoluble in the polymerizable resin, and is optionally filled with inorganic filler. The filler is preferably generally non-toxic and suitable for use in the mouth. The filler can be radiopaque, radiolucent, or non-radiopaque. Fillers as used in dental applications are typically ceramic in nature.

Examples of suitable inorganic fillers are naturally occurring or synthetic materials such as quartz, nitrides (e.g., silicon nitride), glasses derived from, for example Ce, Sb, Sn, Zr, Sr, Ba, or Al, colloidal silica, feldspar, borosilicate glass, kaolin, talc, titania, and zinc glass, zirconia-silica fillers; and low Mohs hardness fillers such as those described in U.S. Pat. No. 4,695,251 (Randklev).

Examples of suitable organic filler particles include filled or unfilled pulverized polycarbonates, polyepoxides, and the like. Preferred filler particles are quartz, submicron silica, and non-vitreous microparticles of the type described in U.S. Pat. No. 4,503,169 (Randklev). Mixtures of these fillers can also be used, as well as combination fillers made from organic and inorganic materials.

Optionally, the surface of the filler particles may be treated with a surface treatment, such as a silane-coupling agent, in order to enhance the bond between the filler and the resin system. The coupling agent may be functionalized with reactive curing groups, such as acrylates, methacrylates, and the like.

The filler particles used to impart a noncovalent structure can be composed of silica, alumina, zirconia, titania, or mixtures of these materials with each other or with carbon. In their synthesized state, these materials are commonly hydrophilic, due to the presence of surface hydroxyl groups. However, the materials may also be modified by treatment with appropriate agents, such as alkyl silanes, in order to modify this character. For example, the surface of a filler particle may be rendered neutral, hydrophobic, or reactive, depending on the desired properties. Fumed silica is a preferred compound for imparting self-supporting character, due to its low cost, commercial availability, and wide range of available surface character.

Preferably, the total amount of filler system is greater than 50 wt-%, more preferably, greater than 60 wt-%, and most preferably, greater than 70 wt-%, based on the total weight of the composition. If the filler system includes fibers, the fibers are present in an amount of less than 20 wt-%, based on the total weight of the composition. Preferably, the total amount of filler system is no more than about 95 wt-%, and more preferably, no more than about 80 wt-%, based on the total weight of the composition. Significantly, such high filler loadings with the resin systems of the present invention is unexpected, particularly in providing a malleable composition.

Initiator System

The compositions of the present invention also contain an initiator system, i.e., one initiator or a mixture of two or more initiators, which are suitable for hardening (e.g., polymerizing and/or crosslinking) of the resin system. The initiators are preferably free radical initiators, which may be activated in a variety of ways, e.g., heat and/or radiation. Thus, for example, the initiator system can be a thermal initiator system (e.g., azo compounds and peroxides), or a photoinitiator system. Preferably, the initiator system includes one or more photoinitiators. More preferably, the initiator system includes at least one photoinitiator active in the spectral region of about 300 nanometers (nm) to about 1200 nm and capable of promoting free radical polymerization and/or crosslinking of ethylenically unsaturated moieties upon exposure to light of suitable wavelength and intensity. A wide variety of such photoinitiators can be used. The photoinitiator preferably is soluble in the resin system. Preferably, they are sufficiently shelf stable and free of undesirable coloration to permit storage and use under typical dental operatory and laboratory conditions. Visible light photoinitiators are preferred.

One type of suitable initiator (i.e., initiator system) is described in U.S. Pat. No. 5,545,676 (Palazzotto et al.), which includes a three component or ternary photoinitiator system. This system includes an iodonium salt, e.g., a diaryliodonium salt, which can be a simple salt (e.g., containing an anion such as $Cl^-$, $Br^-$, $I^-$, or $C_2H_5SO_3^-$) or a metal complex salt (e.g., containing $SbF_5OH^-$ or $AsF_6^-$). Mixtures of iodonium salts can be used if desired. The second component in this ternary photoinitiator system is a sensitizer, which is capable of light absorption within the range of wavelengths of about 400 nm to about 1200 nm. The third component in this ternary photoinitiator system is an electron donor and includes amines (including aminoaldehydes and aminosilanes or other amines as described for the first initiator system), amides (including phosphoramides), ethers (including thioethers), ureas (including thioureas), ferrocene, sulfinic acids and their salts, salts of ferrocyanide, ascorbic acid and its salts, dithiocarbamic acid and its salts, salts of xanthates, salts of ethylene diamine tetraacetic acid and salts of tetraphenylboronic acid.

Examples of sensitizers suitable for use in a ternary photoinitiator system include ketones, coumarin dyes (e.g., ketocoumarins), xanthene dyes, acridine dyes, thiazole dyes, thiazine dyes, oxazine dyes, azine dyes, aminoketone dyes, porphyrins, aromatic polycyclic hydrocarbons, p-substituted aminostyryl ketone compounds, aminotriaryl methanes, merocyanines, squarylium dyes, and pyridinium dyes. Ketones (e.g., monoketones or alpha-diketones), ketocoumarins, aminoarylketones, and p-substituted aminostyryl ketone compounds are preferred sensitizers. Examples of particularly preferred visible light sensitizers include camphorquinone, glyoxal, biacetyl, 3,3,6,6-tetramethylcyclohexanedione, 3,3,7,7-tetramethyl-1,2-cycloheptanedione, 3,3,8,8-tetramethyl-1,2-cyclooctanedione, 3,3,18,18-tetramethyl-1,2-cyclooctadecanedione, dipivaloyl, benzil, furil, hydroxybenzil, 2,3-butanedione, 2,3-pentanedione, 2,3-hexanedione, 3,4-hexanedione, 2,3-heptanedione, 3,4-heptanedione, 2,3-octanedione, 4,5-octanedione, and 1,2-cyclohexanedione. Of these, camphorquinone is the most preferred sensitizer.

Yet another type of photoinitiator includes acylphosphine oxides, such as those described in European Pat. Application No. 173567 (Ying). Suitable acylphosphine oxides are preferably of the general formula $(R^4)_2{-}P({=}O){-}C({=}O){-}R^5$, wherein each $R^4$ is individually a hydrocarbon group, preferably an alkyl group, alicyclic group, aryl group, and aralkyl group, any of which can be substituted with a halo-, alkyl- or alkoxy-group, or the two $R^4$ groups can be joined to form a ring along with the phosphorous atom, and wherein $R^5$ is a hydrocarbon group, preferably, a S-, O-, or N-containing five- or six-membered heterocyclic group, or a $-Z-C({=}O)-P({=}O)-(R^4)_2$ group, wherein Z represents a divalent hydrocarbon group such as alkylene or phenylene having from 2 to 6 carbon atoms. Examples of suitable acylphosphine oxides include bis(2,4,6-trimethylbenzoyl)phenyl phosphine oxide, for example. Optionally, tertiary amine reducing agents may be used in combination with an acylphosphine oxide. Illustrative tertiary amines useful in the invention include those described above as well as ethyl 4-(N,N-dimethylamino)benzoate and N,N-dimethylaminoethyl methacrylate.

Mono- and di-ketones can also be used as photoinitiators. Examples of such systems are described in U.S. Pat. No. 4,071,424 (Dart et al.).

Still another class of photoinitiators includes ionic dye-counterion complex initiators that include a borate anion and a complementary cationic dye. Borate anions useful in these photointiators generally can be of the formula $B(R^6)_4^-$ wherein each $R^6$ is independently an alkyl, aryl, alkaryl, allyl, aralkyl, alkenyl, alkynyl, alicyclic, and saturated or unsaturated heterocyclic groups. Cationic counterions can be cationic dyes, quaternary ammonium groups, transition metal coordination complexes, and the like. Cationic dyes useful as counterions can be cationic methine, polymethine, triarylmethine, indoline, thiazine, xanthene, oxazine or acridine dyes. Quaternary ammonium groups useful as counterions can be trimethylcetylammonium, cetylpyridinium, and tetramethylammonium. Other organophilic cations can include pyridinium, phosphonium, and sulfonium. Cationic transition metal coordination complexes that may be useful as counterions can be complexes of cobalt, ruthenium, osmium, zinc, iron, and iridium with ligands such as pyridine, 2,2'-bipyridine, 4,4'-dimethyl-2,2'-bipyridine, 1,10-phenanthroline, 3,4,7,8-tetramethylphenanthroline, 2,4,6-tri(2-pyridyl-s-triazine) and related ligands. Borate salt photoinitiators are described, for example, in U.S. Pat. Nos. 4,772,530 (Gottschalk et al.), 4,954,414 (Adair et al.), 4,874,450 (Gottschalk), 5,055,372 (Shanklin et al.), and 5,057,393 (Shanklin et al.).

Preferred visible light-induced initiators include camphorquinone combined with a suitable hydrogen donor (e.g., an amine such as those described above for the first initiator system), and optionally a diaryliodonium simple or metal complex salt, chromophore-substituted halomethyl-s-triazine, or halomethyl oxadiazole. Particularly preferred visible light-induced photoinitiators include combinations of an alpha-diketone, e.g., camphorquinone with additional hydrogen donors, and optionally a diaryliodonium salt, e.g., diphenyliodonium chloride, bromide, iodide or hexafluorophosphate.

Preferred ultraviolet light-induced polymerization initiators include ketones, such as benzyl and benzoin, acyloins, and acyloin ethers. Preferred ultraviolet light-induced polymerization initiators include 2,2-dimethoxy-2-phenylacetophenone available under the trade designation IRGACURE 651 and benzoin methyl ether (2-methoxy-2-phenylacetophenone), both from Ciba Speciality Chemicals Corp., Tarrytown, N.Y.

The initiator system is present in an amount sufficient to provide the desired rate of hardening (e.g., polymerizing and/or crosslinking). For a photoinitiator, this amount will be dependent in part on the light source, the thickness of the layer to be exposed to radiant energy, and the extinction coefficient of the photoinitiator. Preferably, the initiator system is present in a total amount of at least about 0.01 wt-%, more preferably, at least about 0.03 wt-%, and most preferably, at least about 0.05 wt-%, based on the weight of the composition. Preferably, the initiator system is present in a total amount of no more than about 10 wt-%, more preferably, no more than about 5 wt-%, and most preferably, no more than about 2.5 wt-%, based on the weight of the composition.

Surfactant System

The compositions of the invention may contain a surfactant system, i.e., one surfactant or a mixture of two or more surfactants. These surfactants, when used in small amounts may interact with other components of the composition, such as an inorganic filler material, to enhance the formation of a non-covalent three-dimensional structure. Such surfactants can be nonionic, anionic, or cationic. The surfactant(s) can be copolymerizable with the resin system or non-copolymerizable. A consideration in the choice of a surfactant that can be used is the degree to which the ingredients of the system are able to participate in hydrogen bonding.

Preferably, the total amount of surfactant system is at least about 0.05 wt-%, more preferably, at least about 0.1 wt-%, and most preferably, at least about 0.2 wt-%, based on the total weight of the composition. Preferably, the total amount of surfactant system is no more than about 5.0 wt-%, more preferably, no more than about 2.5 wt-%, and most preferably, no more than about 1.5 wt-%, based on the total weight of the composition.

Typical nonionic surfactants are usually condensation products of an organic aliphatic or alkylaromatic hydrophobic compound and an alkylene oxide, such as ethylene oxide, which is hydrophilic. The length of the ethylene oxide chain of the condensation product as well as the length of the starting hydrocarbon compound can be adjusted to achieve the desired balance between the hydrophobic and hydrophilic elements. Examples of such surfactants include nonylphenoxypoly (ethyleneoxy) ethanols available under the trade designation IGEPAL CO from Rhone-Poulenc, Cranbury, N.J., and nonylphenyl polyethylene glycol ethers available under the trade designation TERGITOL NP from Dow Chemical Co., Midland, Mich.

Other nonionic surfactants include, but are not limited to, sorbitan fatty acid esters available under the trade designation SPAN from ICI, Runcorn Cheshire, UK, and polyoxyethylene sorbitan fatty acid esters available under the trade designation TWEEN from ICI. Still other satisfactory nonionic surfactants include, but are not limited to, short chain polyfunctional molecules like glycerine, ethylene diamine, ethylene glycol, propylene glycol; and long chain polyfunctional molecules like polyalkylene glycols available under the trade designation UCON from Dow Chemical, polyoxyethylene sorbitol available under the trade designation ATLAS G-2240 from ICI, polyethylene glycols and their methyl ethers available under the trade designation CARBOWAX from Dow Chemical.

Typical cationic surfactants include, but are not limited to, quaternary ammonium salts in which at least one higher molecular weight group and two or three lower molecular weight groups are linked to a common nitrogen atom to produce a cation, and wherein the electrically-balancing anion is selected from the group consisting of a halide (e.g., bromide or chloride), acetate, nitrite, and lower alkosulfate (e.g., methosulfate). The higher molecular weight substituent(s) on the nitrogen is/are often (a) higher alkyl group(s), containing at least about 10 carbon atoms, and the lower molecular weight substituents may be lower alkyl of about 1 to about 4 carbon atoms which may be substituted with hydroxy. One or more of the substituents may include an aryl moiety or may be replaced by an aryl moiety, such as benzyl or phenyl. Among the possible lower molecular weight substituents are also lower alkyls of about 1 to about 4 carbon atoms substituted by lower polyalkoxy moieties such as polyoxyethylene moieties bearing a hydroxyl end group. Examples of useful quaternary ammonium halide surfactants for use in the present invention include, but are not limited to, bis(hydrogenated tallowalkyl) dimethyl quaternary ammonium chloride available under the trade designation ARQUAD 2HT-75 from Akzo Nobel, McCook, Ill., dimethyl di(cocoalkyl) quaternary ammonium chloride available under the trade designation ARQUAD 2C-75 from Akzo Nobel, and N-(tallowalkyl)-1,3-propanediamine dioleate available under the trade designation DUOMEEN TDO from Akzo Nobel.

Typical anionic surfactants include, but are not limited to, dihexyl sodium sulfosuccinate available under the trade designation AEROSOL MA from BASF, Ludwigshafen, Germany, dioctyl sodium sulfosuccinate available under the trade designation ALROWET D-65 from Ciba Speciality Chemicals, the sodium salt of a polymerized carboxylic acid available under the trade designations DAXAD 30 from W. R. Grace, Columbia, Md., TAMOL 731 from Rohm and Haas, Philadelphia, Pa., sodium alkylnaphthalene sulfonate available under the trade designation NEKAL BA-75 from Rohm and Haas, as well as sodium oleate, sodium stearate, sulfated castor oil, zinc hydroxy stearate, all of which are available from a variety of suppliers.

Optional Additives

The composition may additionally include optional agents such as colorants (e.g., pigments conventionally used for shade adjustment), flavorants, medicaments, stabilizers (such as BHT), viscosity modifiers, and the like. Such agents may optionally include reactive functionality so that they will be copolymerized with the resin.

Methods of Use and Products

The compositions of the present invention can be shaped (e.g., molded) into a variety of forms like three-dimensional shapes, preformed sheets, arch-shaped trays, ropes, buttons, woven, or non-woven webs, and the like. The composition can be shaped (to form a first shape) in a variety of ways including, for example, extruding, injection molding, compression molding, thermoforming, vacuum forming, pressing, calendering, and web processing using rollers. Typically, a semi-finished shape is formed using a mold with a positive and negative impression.

The shaped articles can be sold individually or in multiple units, preferably packaged in a way that protects them from heat and/or light that can activate the initiator system contained in the composition.

Generally, a preformed article of appropriate size and shape (the first shape) is selected and custom shaped at a temperature of about 15° C. to 38° C. (preferably, about 20° C. to 38° C., which encompasses typical room temperatures and body temperatures, and more preferably, at room temperature). This shaping can be done by a variety of methods including applying pressure with fingers or an instrument of choice (e.g., hand operation of dental composite instrument), trimming, cutting, sculpting, grinding, etc. Once the desired custom shape has been achieved, the article is hardened (e.g., cured) by exposing it to heat/radiation to cause activation of the initiator system. This can be done either in a single step, or in multiple steps with successive steps of custom shaping being done in-between. One or more of these steps can be carried out in an oxygen-free inert atmosphere or in vacuum. After the final shaping and hardening steps, the hardened article can be further modified in shape by grinding, trimming, etc., if desired. Once the final custom shape of the article has been obtained, it can be polished, painted, or otherwise surface treated, if required for the intended application. Preferably, the final custom shaped articles prepared from the compositions of the present invention do not need an additional veneering material (e.g., a second material that provides a desired appearance or property). The intended application may require mounting, bonding, or otherwise attaching the custom shaped cured article to a second object adhesively, mechanically, or by combination of both.

For the preparation of a provisional dental crown, an appropriate shape and size of a preformed crown is selected and the preformed crown is seated on the prepared tooth to determine the extent of trimming and shaping required, optionally making marks on the crown. The preformed crown is removed from the mouth, the required shape and size adjustments are made by cutting, trimming, shaping, etc., and then re-seated on the tooth preparation where additional shape adjustments are made to provide optimum custom fit, including gingival, lateral, and occlusal fit. The preformed and reshaped crown can then be hardened, typically by exposing it to a dental curing light for a few seconds, if desired, while in the mouth, and then removing it carefully from the mouth and exposing it for final cure to a curing light in a cure chamber, optionally in combination with heat. Alternatively, the crown can also be completely cured in the mouth by irradiating it with a dental curing light. Final adjustments are made by grinding, trimming, etc., if required, and the finished crown is polished and cleaned. The finished crown can then be cemented as is or lined with a suitable resin material prior to placement in the mouth.

This invention also includes a customizable dental impression tray, formed from a self-supporting composition as described herein. Dental trays are commonly used to obtain accurate impressions of a patient's teeth. Commonly, the tray is supplied as a preformed non-customizable item, albeit in a range of sizes. This tray is filled with an impression material (e.g., one or more flowable elastomeric materials, such as polyvinylsiloxane, polyether, or polysulfide) and pressed around the teeth of the upper or lower jaw. The impression material contained within the tray is then cured in place. More accurate impressions can be obtained with increased patient comfort through the use of a customized tray, which can be shaped to fit the patient's mouth more accurately than a generic "one size fits all" tray. Thus, the compositions of the present invention can be used to make a customizable dental impression tray.

One of the major requirements for a dental impression tray is that the impression material adheres to the interior surface of the tray. Due to their shape, a mechanical interlock is typically formed between the teeth and the impression material during curing. Although the impression material may be flexible even after curing, insufficient adhesion will cause the impression material to separate from the tray or tear during removal from the mouth. Current tray technology relies on addition of an adhesive to the tray prior to filling it with impression material in order to create this bond. The present invention allows for this, although a dental impression tray can include at least one structured surface (i.e., a surface having a 3-dimensional structure formed from depressions, holes, protuberences, or the like), which can be a microreplicated surface or be formed by a porous substrate, for example. Such a structured surface provides a mechanical interlock between the surface of the tray and the cured impression material, analogous to that formed between the impression material and the teeth. However, the interlock between the tray and impression material is much more extensive, and thus stronger than the impression material/tooth interface. As such, the requirement for an adhesive is eliminated. This structured surface in the tray may be created in a number of ways, including, but not limited to, molding, embossing, or lamination of a second structured layer such as a porous substrate (e.g., including films, foams, and knit, woven, and nonwoven fabrics). If a second layer is laminated to the base material, said lamination can also contribute in other ways, e.g., through enhancement of mechanical properties.

The hardenable, self-supporting structures (e.g., dental products) of this invention can be prepackaged either individually or as an ensemble. Such packaging material should protect these products from conditions that would activate the initiator system and thus cause premature hardening, e.g., such as could result from exposure to light in the case of a photoinitiator. In addition, the packaging material optionally conforms to the surfaces of the product, thereby providing additional mechanical strength in order to resist damage during shipping. For example, a preformed crown or tray could be packaged in a layer of polyethylene on all sides. The polyethylene provides a mechanical structure and can be sealed to avoid contact with water. If the polyethylene were filled with an appropriate dye, e.g., carbon black, incident light would be absorbed before it could reach the enclosed product. If such a packaging layer is somewhat rigid, and if the packaging material is shaped similar to the preformed article of the invention, then the packaging could enhance the dimensional stability of the preformed product during shipment and storage. In certain cases, the packaging may thus form an integral part of the product system.

The invention is also useful in a number of preformed orthodontic applications. For example, the hardenable composition may be fabricated into a custom appliance such as a lingual retainer, a space retainer, a hook, a button, or a splint. As another example, the composition may be used to make a portion of an appliance, such as a custom base for an orthodontic bracket that is adapted to closely fit the curvature of a patient's tooth, or an orthodontic bracket with tiewings that are oriented at a particular angle to avoid contact with adjacent structure in the oral cavity. The composition also may be used to make a tooth facsimile that is bonded to an archwire to hide open spaces between teeth during the course of treatment. Furthermore, the composition may be used to bond groups of adjacent teeth together to establish strong anchorage for other orthodontic appliances. Additionally, the composition may be formed into a droplet of material that is bonded to an archwire at a certain location to prevent sliding movement of the archwire or to prevent movement of another appliance. When used in orthodontic applications, the composition of the invention can be shaped to a desired configuration in vivo and then hardened in place in the oral cavity. Alternatively, the composition can be shaped to a desired configuration outside of the oral cavity using, if desired, a model of the patient's tooth structure. When the composition is shaped outside of the oral cavity, the composition is preferably hardened before placement in the oral cavity.

EXAMPLES

The following examples are given to illustrate, but not limit, the scope of this invention. Unless otherwise indicated, all parts and percentages are by weight and all molecular weights are weight average molecular weight.

Test Methods

Pre-Cure Elastic and Viscous Moduli (Rheology) Test

Elastic Moduli (G') and Viscous Moduli (G") as an indication of composition rheology were measured according to the following test procedure. A composition sample was heated to 70° C. in an oven and pressed between two Teflon-lined glass plates into a sheet having a thickness of approximately 2 millimeters (mm). After cooling to room temperature and aging for 48 hours, an 8-mm diameter disk was cut from the resulting sheet. Rheological measurements were carried out on a Rheometrics RDA II dynamic mechanical analyzer (Rheometric Scientific, Piscataway, N.J.) using 8-mm parallel plate fixtures. Elastic and Viscous Moduli were measured at 25° C. as a function of frequency (Hz) for the disk of pre-cured composite and results reported in kilopascals (kPa).

Pre-Cure Crown Formation Test

The objective of this test is to determine if a composition could be made into a self-supporting crown and then determine qualitatively if that crown is malleable, shapeable, and trimable at room temperature. A composite sample was manually formed into a 2-mm thick "cup" approximately the size of a molar and was pressed at 85° C. between a positive mold of a slightly reduced maxillary central incisor and a negative mold of 3M ESPE polycarbonate crown #10. The positive and negative molds were prepared from 3M ESPE IMPRINT II Monophase and 3M ESPE EXPRESS STD Putty Material (3M Co., St. Paul, Minn.), respectively. In order for a composition sample to "pass" this Test Method, the pressed crown should easily be removed from the mold after cooling to room temperature without any markable deformation.

The crown sample was further evaluated based on its ability to be custom fitted on a more heavily reduced maxillary central incisor on a TYPODONT arch (Columbia Dentoform, Long Island City, N.Y.). The crown sample was examined for (1) how well it retained its form while being handled, (2) how easily it could be trimmed with scissors, and (3) how well it could be custom-fitted on the central incisor by adapting the crown shape with a composite instrument while positioned on the reduced tooth, without either breaking or demonstrating any elastic deformation. In order for a composition to "pass" this Test Method, the formed crown sample was required to successfully meet each of these three quality parameters.

Pre-Cure Composite Packability Test

The packability of a composite material was qualitatively determined according to the following procedure. The first molar tooth on a lower arch model (SM-PVR-860 from Columbia Dentaform Corporation, Long Island City, N.Y.) was prepared with a mesio occluso cavity preparation. A metal matrix band (dead soft HO Band-Young, type universal #1 from Henry Schein catalog) was fitted around the molar with the help of a Tofflemire matrix retainer (type universal, from Henry Schein catalog). This model was then placed in a small heating chamber, which was kept at a constant temperature of 38° C. Once the model had reached a temperature of 38° C. it was taken out of the heated chamber and a pellet of the composite to be tested was placed in the prepared tooth cavity. Packability of the composite was evaluated by compacting the pellet in the cavity with a double-ended amalgam plugger (1/2 Black DE from Henry Schein catalog). The ability of the composite material to be condensed, rather than flowing around the plugging instrument, was determined. Evaluation also included the ability of the composite material to transfer some of the compacting force to the metal matrix band, and thereby to deform the band. A composite material that both could be condensed in the cavity and that deformed the band was judged to be packable.

Pre-Cure Differential Scanning Calorimetry (DSC) Test

The crystallinity and melting point of samples was determined by differential scanning calorimetry using a DSC 2920 instrument from TA Instruments (New Castle, Del.). A sample weighing 5-10 mg that had been aged for at least 72 hours was placed in a standard aluminum pan and heated at 5° C./min from −40° C. to 120° C. The resulting thermogram was examined for evidence of a melting point range and endothermic peaks that would be associated with the melting of crystalline species. The absence of endothermic peaks would be indicative of no crystalline component in the sample.

Post-Cure Flexural Strength (FS) and Flexural Modulus (FM) Test

Flexural Strength and Flexural Modulus were measured according to the following test procedure. A composition sample was pressed at 65° C. in a preheated mold to form a 2-mm×2-mm×25-mm test bar. The bar was aged at room temperature for 24 hours and light cured for 90 seconds by exposure to two oppositely disposed VISILUX Model 2500 blue light guns (3M Co.). The bar was then post-cured for 180 seconds in a Dentacolor XS unit (Kulzer, Inc., Germany) light box, and sanded lightly with 600-grit sandpaper to remove flash from the molding process. After storing in distilled water at 37° C. for 24 hours, the Flexural Strength and Flexural Modulus of the bar were measured on an Instron tester (Instron 4505, Instron Corp., Canton, Mass.) according to ANSI/ADA (American National Standard/American Dental Association) specification No. 27 (1993) at a crosshead speed of 0.75 mm/minute. Six bars of cured composite were prepared and measured with results reported in megapascals (MPa) as the average of the six measurements.

Post-Cure Compressive Strength (CS) Test

Compressive Strength was measured according to ANSI/ADA Specification No. 27 (1993). Specifically, a composition sample was heated to 85° C., packed into a 4-mm (inside diameter) glass tube, and the tube capped with silicone rubber plugs and compressed axially at approximately 0.28 MPa for 5 minutes. The sample was light cured for 90 seconds by exposure to two oppositely disposed VISILUX Model 2500 blue light guns (3M Co.) and then irradiated for 180 seconds in a Dentacolor XS light box (Kulzer, Inc.). The cured sample was then cut on a diamond saw to form cylindrical plugs 8-mm long for measurement of CS. The plugs were stored in distilled water at 37° C. for 24 hours prior to testing. Measurements were carried out on an Instron tester (Instron 4505, Instron Corp.) with a 10-kilonewton (kN) load cell. Five plugs of cured composite were prepared and measured with results reported in MPa as the average of the five measurements.

Post-Cure Diametral Tensile Strength (DTS) Test

Diametral Tensile Strength was measured according to ANSI/ADA specification No. 27 (1993). A composition sample was compressed in a glass tube and cured as described above for the Compressive Strength Test. The cured sample was then cut into discs 2.2-mm long for measurement of DTS. The disks were stored in water as described above and measured with an Instron tester (Instron 4505, Instron Corp.) with a 10-kN load cell at a crosshead speed of 1 meter/minute. Five discs of cured composite were prepared and measured with results reported in MPa as the average of the five measurements.

Abbreviations/Definitions

| BHT | 2,6-Di-tert-butyl-4-methylphenol (Sigma-Aldrich Fine Chemicals, St. Louis, MO) |
|---|---|
| BisGMA | 2,2-Bis[4-(2-hydroxy-3-methacryloyloxypropoxy)phenyl]propane CAS No. 1565-94-2 |
| CPQ | Camphorquinone (Sigma-Aldrich) |
| EDMA | Ethyl 4-(N,N-dimethylamino)benzoate (Sigma-Aldrich) |
| M5 | Hydrophilic fumed (pyrogenic) silica (Cab-O-Sil M5, Cabot Corp. Tuscola, IL) |
| R711 | Methacryl silane-treated fumed (pyrogenic) silica (AEROSIL R-711, Degussa Corp., Parsippany, NJ) |
| R972 | Hydrophobic fumed (pyrogenic) silica (AEROSIL R-972, Degussa Corp.) |
| ARQ | Cationic surfactant ARQUAD 2HT-75 (Akzo Nobel Chemicals, Inc., McCook, IL) |
| TPEG | Nonionic surfactant Carbowax TPEG 990 (Dow, Midland, MI) |
| STZ | Silane-Treated $ZrO_2/SiO_2$ prepared as described in U.S. patent application Ser. No. 09/541,417, abandoned in favor of U.S. Pat. No. 6,624,211, issued on Sept. 23, 2003 (Karim) |
| IEM | 2-Isocyanatoethyl methacrylate (Sigma-Aldrich) |
| TONE 0230 Diol | Hydroxy-terminated polycaprolactone (Dow) |
| TONE 0230-IEM | Reaction product between TONE 0230 Diol and IEM; prepared as described in U.S. patent application Ser. No. 08/896,549, issued as U.S. Pat. No. 6,506,816 on Jan. 14, 2003 (Aasen et al.) |
| MAA | Methacrylic anhydride (Sigma-Aldrich) |
| PE-Diol | Polyethylene diol (MW approximately 2500, Sigma-Aldrich) |
| THF | Tetrahydrofuran |
| Polyol PP50 | Pentaerythritol ethoxylate (Perstorp Speciality Chemicals, Toledo, OH) |

-continued

| HEMA | 2-Hydroxyethyl methacrylate (Sigma-Aldrich) |
|---|---|
| DBU | 1,8-Diazabicycol[5.4.0]undec-7-ene (Sigma-Aldrich) |
| Oligo VDM | Vinyl dimethylazlactone oligomer, prepared as described in Example 65 of U.S. patent application Ser. No. 09/884173, issued as U.S. Pat. No. 6,635,690 on Oct. 21, 2003 (Abuelyaman et al.) |
| UDMA | Diurethane dimethacrylate (ROHAMERE 6661-0, Monomer Polymer and Dajae Labs, Inc., Feasterville, PA) |
| BisEMA-6 | Six-mole ethoxylated bisphenol A dimethacrylate (Sartomer CD541, Sartomer Co., Exton, PS) |
| TEGDMA | Triethyleneglycol dimethacrylate (Sartomer Co.) |
| DPIHFP | Diphenyl Iodonium Hexafluorophosphate (Johnson Matthey, Alpha Aesar Division, Ward Hill, NJ) |
| Benzotriazole | 2-(2-Hydroxy-5-methacrylyoxyethylphenyl)-2H-benzotriazole (Ciba Specialty Chemicals, Terrytown, NJ) |
| LEX110 | Lexorez-1150-110 polyester polyol (Inolex Chemical Co., Philadelphia, PA) |
| LEX160 | Lexorez-1150-160 polyester polyol (Inolex Chemical Co.) |
| LEX110-IEM | Reaction product between Lexorez-1150-110 and IEM; prepared as described herein |
| LEX160-IEM | Reaction product between Lexorez-1150-160 and IEM; prepared as described herein |
| THEIC-TMA | Tris(2-hydroxyethyl) isocyanurate triacrylate (SR 368, Sartomer Co.) |
| THEIC-TA | Tris(2-hydroxyethyl) isocyanurate triacrylate (SR 290, Sartomer Co.) |
| CHDM-DMA | Cyclohexane dimethanol dimethacrylate (CD 401, Sartomer Co.) |
| THEI(5)-IEM | Reaction product (1:15:3 molar ratio) of 1,3,5-tris(2-hydroxyethyl)cyanuric acid with caprolactone and IEM prepared as described herein |
| THEI(10)-IEM | Reaction product (1:30:3 molar ratio) of 1,3,5-tris(2-hydroxyethyl)cyanuric acid with $\epsilon$-caprolactone and IEM prepared as described herein |
| BisGMA(5)-IEM | Reaction product (1:10:2 molar ratio) of BisGMA with $\epsilon$-caprolactone and IEM prepared as described herein |
| GGDA(5)-IEM | Reaction product (1:15:3 molar ratio) of Glycerol 1,3-diglycerolate diacrylate with $\epsilon$-caprolactone and IEM prepared as described herein |

Starting Materials

Resin A

Polyethylene diol (PE-Diol, 25 grams (g)) and methacrylic anhydride (4.0 ml, Sigma-Aldrich) were added to a round-bottom flask along with BHT (0.02 g) to scavenge free radicals. The flask was purged with nitrogen for 10 minutes, and then heated with stirring overnight at 100° C. The resulting material was poured into methanol, recovered by filtration, dissolved in hot toluene, reprecipitated with methanol, again recovered by filtration, and dried overnight on a vacuum line. The dried solid was designated Resin A. Analysis by $^1$H NMR indicated complete conversion of the diol to methacrylate functionality.

Resin B

A 58% by weight solution of octadecyl acrylate (Sigma-Aldrich) in ethyl acetate (82 g of solution), HEMA (2.5 g) and toluene (50 g) were charged into a 3-neck reaction vessel equipped with magnetic stirring, a water-cooled condenser, a thermocouple and a nitrogen inlet. The solution was heated under nitrogen to 115° C. and, with stirring, tert-butylperoxybenzoate (0.1 g, Sigma-Aldrich) dissolved in toluene (3 g) was charged into the vessel. A small exotherm (temperature increase of approximately 3-5° C.) was observed. After 30 minutes, 3.34 g of IEM in the presence of a catalytic amount of dibutyltin dilaurate (0.68 g, Sigma-Aldrich) was added in order to functionalize the pendant hydroxyl units of the resin. The resulting mixture was agitated overnight in a 60° C.

shaker bath. The resulting methacrylate functional resin was isolated by precipitation with methanol and subsequent filtration. The dried solid was designated Resin B. The methacrylate functionalization was confirmed by crosslinking a mixture of the HEMA-IEM adduct and isooctyl acrylate in the presence of a photoinitiator, DAROCUR 1173 (Ciba-Geigy, Hawthorn, N.Y.), and exposure to UV light.

Resin C

A polycaprolactone 4-arm star resin was prepared according to the following procedure. Polyol PP50 (35.6 g, 0.1 mole (mol)) and ε-caprolactone (320.0 g, 2.8 mol, Sigma-Aldrich) were added to a glass vessel and heating under nitrogen to 110° C. FASTCAT 4224 (0.21 g, 0.5 millimole (mmol), Atofina Chemicals, Inc., Philadelphia, Pa.) was added and the mixture was heated at 170° C. for five hours. After cooling, a tan, solid (melting point 48-52° C.) was formed, collected by filtration, and dried. The solid had an OH equivalent weight of 709. A portion of the solid (50.0 g, 18 mmol) was mixed with methacrylic anhydride (11.09 g, 72 mmol, Sigma-Aldrich) and BHT (0.35 g, 1.6 mmol). After heating at 100° C. for 17 hours and cooling to room temperature, a tan solid was obtained. The dried solid was designated Resin C.

Resin D

To a stirred solution of OligoVDM (25 g, $1.7 \times 10^{-1}$ mol) and THF (250 ml) under nitrogen were added octadecyl alcohol (29.7 g, $1.1 \times 10^{-1}$ mol), HEMA (1.5 g, $1.2 \times 10^{-2}$ mol), and DBU (0.2 g, $1.3 \times 10^{-3}$ mol). The resultant suspension was heated to 40° C. and maintained at this temperature with stirring overnight for approximately 12 hours. The resulting yellow-orange viscous liquid was isolated by pouring into methanol and evaporation of the methanol/THF solvent at 80° C. for 12 hours under a vacuum. The dried material was designated Resin D.

THEI(10)-IEM

In a 250-ml 3-neck flask equipped with a mechanical stirrer under nitrogen atmosphere, 1,3,5-tris(2-hydroxyethyl)cyanuric acid (4.30 g, 0.016 mol) was suspended in ε-caprolactone (54.70 g, 0.48 mol) with a continuous stirring. A few drops of tin(II) ethyl hexanoate were added and the mixture was heated at 130-150° C. overnight. A clear yellow liquid was obtained. The reaction temperature was lowered to 50° C. and then BHT (50 mg) was added followed by 5 drops of dibutyltin dilaurate. IEM (7.66 g, 0.049 mol) was then charged at 50° C. over 45 minutes. After 20 minutes of stirring, the heat was turned off. The liquid solidified into a material that was characterized by IR, NMR and GPC. (Mw=6.46E+03, Mn=5.69E+03, P=1.14)

THEI(5)-IEM

This product was prepared as described for THEI(10)-IEM, except the amount of ε-caprolactone was halved to 27.35 g, 0.24 mol. The resulting product was isolated as a solid that was characterized by IR, NMR and GPC. (Mw=4.36E+03, Mn=2.859E+03, P=1.53)

BisGMA(5)-IEM

This product was prepared as described for THEI(10)-IEM, but utilizing a dry air atmosphere and the reactants Bis GMA (18.50 g, 0.036 mol), ε-caprolactone (42.10 g, 0.369 mol), and IEM (11.6 g, 0.074 mol). The resulting product was isolated as a solid that was characterized by IR and NMR.

GGDA(5)-IEM

This product was prepared as described for BisGMA(5)-IEM, but utilizing a dry air atmosphere and the reactants glycerol 1,3-diglycerolate diacrylate (triglycerol diacrylate), ε-caprolactone, and IEM. The resulting product was isolated as a solid.

LEX110-IEM

A mixture of 20.0 g (20 mmol) LEXOREZ-1150-110, 6.24 g (40 mmol) 2-isocyanatoethyl methacrylate, 70 g acetone, and 0.03 g (0.05 mmol) dibutyltin dilaurate was heated to 50° C. for 5 hours. The solvent was then removed under reduced pressure to provide the product as a white solid.

LEX160-IEM

A mixture of 20.0 g (28 mmol) LEXOREZ-1150-160, 8.57 g (55 mmol) 2-isocyanatoethyl methacrylate, 70 g acetone, and 0.03 g (0.05 mmol) dibutyltin dilaurate was heated to 50° C. for 5 hours. The solvent was then removed under reduced pressure to provide the product as a white solid.

Examples 1-14 and Comparative Example 1 (CE-1)

Self-Supporting Light-Curable Composites

Self-supporting, light-curable composites (Examples 1-14 and Comparative Example 1) were prepared according to the following procedure. The photoinitiator components were initially dissolved in bisGMA, UDMA, or bisGMA/UDMA/bis-EMS6/TEGDMA blend in a water bath. Then the ingredients (names and quantities for each example shown in Table 1) were weighed into a MAX 20 plastic mixing cup having a screw cap (Flakteck, Landrum, S.C.) and the closed cup heated in an oven at 85° C. for 30 minutes. The cup was placed in a DAC 150 FV speed mixer (Flakteck) and spin mixing carried out for 1 minute at 3000 rpm. The cup was then reheated for 30 minutes at 85° C. followed by another minute of mixing at 3000 rpm to afford the final blended composite. A similar blended composite was made without the photoinitiators (CPQ and EDMA) for ease of pre-cure physical property testing.

TABLE 1

| Ex. | Bis GMA (g) | Resin Additive (Semi-Crystalline) (g) | Surfactant-(g) Fumed Silica-(g) | STZ (g) | CPQ (phr*) | EDMA (phr) |
|---|---|---|---|---|---|---|
| CE-1 | 4.0 | — | — | 16.0 | 0.25 | 1.0 |
| 1 | 3.8 | — | ARQ-0.2 R972-0.2 | 15.8 | 0.25 | 1.0 |
| 2 | 2.0 | TONE0230-IEM-2.0 | — | 16.0 | 0.25 | 1.0 |
| 3 | 2.0 | TONE0230-IEM-2.0 | ARQ-0.12 M5-0.2 | 15.80 | 0.25 | 1.0 |
| 4 | 2.99 | TONE0230-IEM-1.0 | TPEG-0.12 M5-0.2 | 15.72 | 0.25 | 1.0 |
| 5 | 1.0 | TONE0230-IEM-2.99 | TPEG-0.12 M5-0.2 | 15.72 | 0.25 | 1.0 |

TABLE 1-continued

| Ex. | Bis GMA (g) | Resin Additive (Semi-Crystalline) (g) | Surfactant-(g) Fumed Silica-(g) | STZ (g) | CPQ (phr*) | EDMA (phr) |
|---|---|---|---|---|---|---|
| 6 | 2.8 | Resin A-1.2 | — | 16.0 | 0.175 | 0.7 |
| 7 | 3.0 | Resin B-1.0 | — | 16.0 | 0.188 | 0.75 |
| 8 | 2.0 | Resin C-2.0 | — | 16.0 | 0.125 | 0.5 |
| 9 | 1.99 | Resin C-1.99 | TPEG-0.12 M5-0.2 | 15.72 | 0.125 | 0.5 |
| 10 | 3.0 | Resin D-1.0 | — | 16.0 | 0.188 | 0.75 |
| 11 | 3.8 | — | ARQ-0.2 | 16.0 | 0.25 | 1.0 |
| 12 | 1.9 | TONE0230-IEM-1.9 | TPEG-0.2 | 16.0 | 0.25 | 1.0 |
| 13 | 2.0 | TONE0230-IEM-2.0 | M5-0.2 | 15.8 | 0.25 | 1.0 |
| 14 | — | TONE0230-IEM-4.0 | — | 16.0 | 0.25 | 1.0 |
| 15 | 2.4** | TONE0230-IEM-5.6 | TPE-0.24 M5-0.4 | 11.5 | 0.25 | 1.0 |

*phr - Parts per hundred parts of resin (resin = BisGMA + Resin Additive)
**In Example 15, UDMA was used in place of BisGMA

Example 15

Dental Impression Tray Preparation and Simulated Use

A self-supporting, light-curable composite was prepared according to the procedure described in Examples 1-14 with the names and quantities for each ingredient used in this Example 15 shown in Table 1.

The bulk composite was pressed in a Carver press between two siliconized paper liners (TPK 7120, 3M Co.) to a thickness of approximately 2 mm and heated to 40° C. The two paper liners were discarded and the sheet was laminated manually under hand pressure at 40° C. between two layers of a nonwoven fabric (SONTARA 8010, DuPont, Old Hickory, Tenn.). While still warm, a 10-cm×10-cm sheet of the resulting laminate was placed over a stone model of a lower jaw, shaped to fit the contour loosely, and allowed to cool down to room temperature overnight. The contoured form was carefully removed from the model and cut into the shape of an impression tray including a handle to provide a self-supporting, malleable and curable custom tray.

After several days of storage at room temperature the use of the custom tray was simulated on the stone model of the lower jaw. Several layers of wet Kleenex tissue paper were first placed along the complete arch, followed by placing the custom tray on top. Custom fitting was easily achieved by applying simple finger pressure along the whole length of the tray. Then the tray was tack cured for 20 seconds with a VISILUX Model 2500 curing light (3M Co.), followed by further cure for 180 seconds in a Dentacolor XS unit (Kulzer, Inc.). A hard, rigid, tough tray was thereby obtained.

This tray was then filled with Imprint II Monophase Impressioning Material (3M Co.) and pressed against the stone model (without the layer of the tissue paper) and retained in place until the impression material hardened. At this point the tray, together with the hardened impression material, was separated from the stone model to obtain the impression of the whole arch. Excellent adhesion was observed between the hardened impression material and the non-woven surface of the tray.

Examples 16-32

Self-Supporting Light-Curable Composites

Self-supporting, light-curable composites (Examples 16-32) were prepared according to the procedure described for Examples 1-14 with the ingredient names and quantities for each example shown in Table 2).

TABLE 2

| Ex. | Bis GMA (g) | Resin Additive (Semi-Crystalline) (g) | Surfactant-(g) Fumed Silica-(g) | STZ (g) | Photo-initiator |
|---|---|---|---|---|---|
| 16 | 1.95 | LEX160-IEM-1.95 | TPEG-0.12 M5-0.468 | 15.13 | PI#1** |
| 17 | 2.93 | LEX110-IEM-0.98 | TPEG-O.12 M5-0.468 | 15.13 | PI#1 |
| 18 | 2.7* | TONE0230-IEM-0.9 | ARQ-0.11 R972-0.54 | 14.80 | PI#2*** |
| 19 | 2.52 | TONE0230-IEM-1.18 | TPEG-0.11 R711-0.44 | 14.36 | PI#2 |
| 20 | 2.93 | THEI(10)-IEM-0.98 | TPEG-0.12 M5-0.39 | 15.21 | PI#1 |
| 21 | 1.95 | THEI(5)-IEM-1.95 | TPEG-0.12 M5-0.468 | 15.13 | PI#1 |
| 22 | 1.99 | BisGMA(5)-IEM-1.99 | TPEG-0.12 M5-0.20 | 15.72 | PI#1 |
| 23 | 1.99 | GGDA(5)-IEM-1.99 | TPEG-0.12 M5-0.20 | 15.72 | PI#1 |
| 24 | 2.93 | THEIC-TMA-0.98 | TPEG-0.12 M5-0.468 | 15.13 | PI#1 |

TABLE 2-continued

| Ex. | Bis GMA (g) | Resin Additive (Semi-Crystalline) (g) | Surfactant-(g) Fumed Silica-(g) | STZ (g) | Photo-initiator |
|---|---|---|---|---|---|
| 25 | 1.95 | THEIC-TA-1.95 | TPEG-0.12 M5-0.468 | 15.13 | PI#1 |
| 26 | 2.93 | THEIC-TA-0.98 | TPEG-0.12 M5-0.468 | 15.13 | PI#1 |
| 27 | 2.52* | CHDM-DMA-1.08 | TPEG-0.11 M5-0.432 | 14.90 | PI#2 |
| 28 | 3.50* | None | TPEG-0.11 M5-0.4375 | 14.47 | PI#2 |
| 29 | 3.50* | None | TPEG-0.11 M5-0.5250 | 14.39 | PI#2 |
| 30 | 3.24* | TONE0230-IEM-0.36 | TPEG-0.11 M5-0.18 | 15.16 | PI#2 |
| 31 | 3.24* | TONE0230-IEM-0.36 | TPEG-0.11 M5-0.45 | 14.89 | PI#2 |
| 32 | 3.24* | THEI(10)-IEM-0.36 | TPEG-0.11 M5-0.36 | 14.89 | PI#2 |

*In Examples 18 and 27-32, a resin blend was used in place of BisGMA. The blend consisted of BisGMA (25%), UDMA (35%), BisEMA-6 (35%), and TEGDMA (5%).
**PI#1 - Blend of CPQ (0.25 phr) and EDMA (1.0 phr) [phr - parts per 100 parts of bis-GMA and semi-crystalline resin).
***PI#2 - Blend of CPQ (0.176 phr), EDMA (1.55 phr), DPIHFP (0.517 phr), BHT (0.155 phr), and Benzotriazole (1.552 phr).

Sample Evaluations

Examples 1-14, 16-32, and Comparative Example 1

Composite samples (Examples 1-14, 16-32, and Comparative Example 1) were evaluated for pre-cure elastic and viscous moduli, for pre-cure crown formation, and for post-cure flexural strength, flexural modulus, compressive strength, and diametral tensile strength according to the Test Methods described herein. All samples passed the Pre-Cure Crown Formation Test, except for the Comparative Example 1 sample that was very soft and not self-supporting. Results from the other evaluations are provided in Table 3 (Examples 1-14 and Comparative Example 1) and Table 4 (Examples 16-32).

Figure 2:
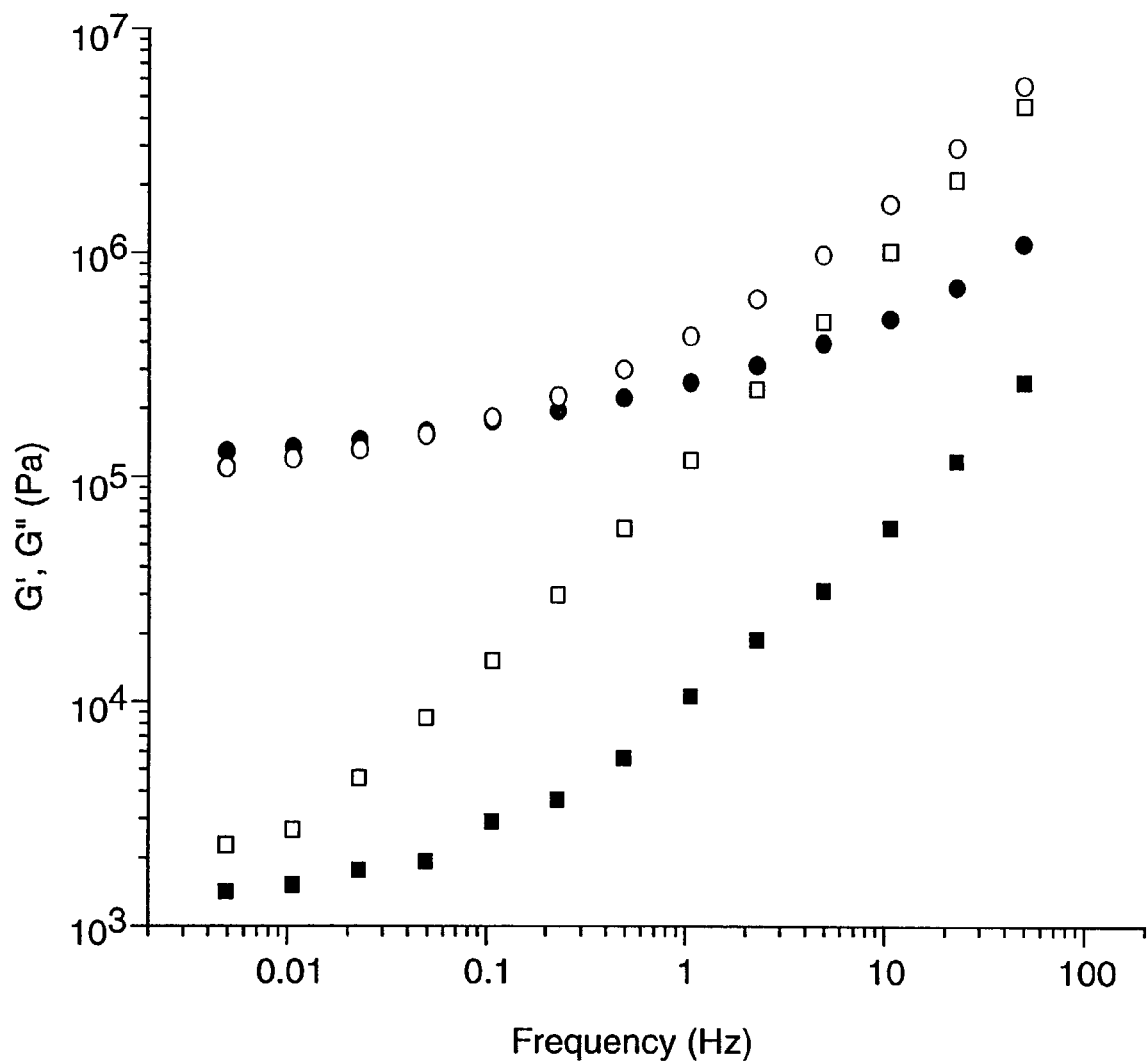
FIG. 2. Rheology of Comparative Example 1 (squares) and Example 1 (circles). Solid symbols represent G', while open symbols represent G".

Example 1, in comparison with Comparative Example 1, shows that the addition of fumed silica and surfactant to the bisGMA significantly increased the elastic and viscous moduli of the resulting composite and thereby changed the physical nature of the composite from very soft to self-supporting. As shown in FIG. 2, the elastic and viscous moduli (G' and G", respectively) are increased from approximately $10^{-3}$ (for Comparative Example 1) to approximately $10^5$ Pascals (Pa) (for Example 1). This suggests that the Example 1 composite has properties at room temperature more similar to those of the dental baseplate wax shown in FIG. 1. Furthermore, the frequency dependence of the moduli of Example 1 is reduced, indicative of a more solid-like character similar to that of the dental waxes. It is noted that unlike a dental wax that transforms above its melting point to a free-flowing liquid, the compositions of the present invention soften, but do

TABLE 3

(Numbers in Parentheses are Standard Deviations)

| Ex. | G' kPa (at 0.005 Hz) | G" kPa (at 0.005 Hz) | Flexural Strength, MPa | Compressive Strength, Mpa | Diametral Tensile Strength, MPa | Flexural Modulus, MPa |
|---|---|---|---|---|---|---|
| CE-1 | 1.4 | 2.3 | 133(21) | 277(26) | 44(6) | 7933(805) |
| 1 | 127 | 108 | 134(15) | 323(13) | 42(6) | 8487(678) |
| 2 | 95 | 80 | 115(12) | 340(19) | 52(11) | 5275(630) |
| 3 | 577 | 350 | 121(12) | 319(21) | 44(6) | 5169(726) |
| 4 | 138 | 120 | 168(13) | 328(38) | 42.5(7) | 8928(194) |
| 5 | 3080 | 2410 | 122(10) | 284(16) | 26(8) | 4551(449) |
| 6 | 624 | 303 | 109(7) | 171(25) | 28(2) | 5146(356) |
| 7 | 1890 | 947 | 107(18) | 263(13) | 24(3) | 7359(777) |
| 8 | 213 | 156 | 79(15) | 298(12) | 42(4) | 3410(354) |
| 9 | 557 | 357 | 87(8) | 272(31) | 46(13) | 3121(224) |
| 10 | 268 | 203 | 85(25) | 233(12) | 33(8) | 5688(1069) |
| 11 | 88 | 73 | 120(4) | 299(12) | 39(7) | 6429(608) |
| 12 | 232 | 146 | 86(12) | 356(6) | 54(7) | 3943(204) |
| 13 | 520 | 224 | 137(8) | 318(22) | 45(10) | 5430(742) |
| 14 | 2120 | 1610 | 76(10) | 296(16) | 45(16) | 1960(363) | not become free-flowing fluids (i.e., liquids) above their melting points or melting ranges.

Examples 2-5, in comparison with Comparative Example 1, show that the addition of TONE 0230-IEM light-curable polymer to the bisGMA significantly increased the elastic and viscous moduli of the resulting composite and thereby changed the physical nature of the composite from very soft to self-supporting. Additionally, it can be concluded from the results in Table 3 that further addition of surfactant/fumed silica ingredients increases the moduli, and that the moduli increases with increasing amounts of TONE 0230-IEM polymer. It is theorized that these enhanced properties are due to the crystalline nature of the TONE 0230-IEM polymer.

Examples 6-10, in comparison with Comparative Example 1, show that the addition of other types of polymers (Polymers A-D) can be added to the bisGMA in order to significantly increase the elastic and viscous moduli of the resulting composite in the same way that was achieved with the TONE 0230-IEM polymer. Comparison of Examples 8 and 9 shows the positive effect on moduli of adding a surfactant/fumed silica ingredient.

Example 11, in comparison with Comparative Example 1, shows that elastic and viscous moduli can be significantly increased by the addition of surfactant ARQ alone (with no Polymer Additive) to the bisGMA.

Examples 12-13, in comparison with Comparative Example 1, show that elastic and viscous moduli can be significantly increased by the addition of TONE 0230-IEM polymer plus surfactant TPEG (Example 12) or plus fumed silica M5 (Example 13) to the bisGMA.

Example 14, in comparison with Comparative Example 1, shows that elastic and viscous moduli can be significantly increased by the utilization of high levels TONE 0230-IEM polymer alone (with no BisGMA). Following curing, all samples (Examples 1-14) were converted into a hard, tough material having adequate flexural modulus and flexural strength, compressive strength, and diametral tensile strength to be useful as a dental article, e.g., as a dental crown.

It can be concluded from the results shown in Table 4 that, following curing, all samples (Examples 16-32) were converted into a hard, tough material having adequate flexural modulus and flexural strength, compressive strength, and diametral tensile strength to be useful as a dental article, e.g., as a dental crown.

Sample Evaluations (Crystallinity and Packability)

In addition to the testing results provided in Tables 3 and 4; Examples 2, 3, 13, 14, 24, 25, and 26; and the commercial material REVOTEK LC Resin (GC Dental Products Corp., Japan) were confirmed to contain a crystalline component having a melting point above 20° C. when evaluated according to the Pre-Cure DSC Test Method described herein. A sample of the commercial material SUREFIL High Density Posterior Restorative (Dentsply) showed the presence of a crystalline component having a melting point below 20° C. That is, there is no crystalline component as defined herein. In contrast, DSC evaluations of Example 1 and the commercial materials PRODIGY Condensable Composite Restorative System (Kerr, Orange, Calif.) and TRIAD Visible Light Cure Provisional Material (Dentsply Caulk, Milford, Del.) suggested the absence of any crystalline component. The results of these DSC measurements are provided in Table 5. The Elastic Moduli (G') and Viscous Modulit (G") of the four commercial materials (according to the Test Method provided herein, except that samples were pressed without heating) are also provided in Table 5.

TABLE 5

| Example | G' kPa (at 0.01 Hz) | G" | Melting Point Range (° C.) (Peak Exotherm (° C.)) | Crystalline Component (at 22° C.) |
|---|---|---|---|---|
| 1 | NM* | NM | No Melting Point | No |
| 2 | NM | NM | 27-43 (36.9) | Yes |
| 3 | NM | NM | 29-43 (36.9) | Yes |
| 13 | NM | NM | 27-43 (37.4) | Yes |

TABLE 4

(Numbers in Parentheses are Standard Deviations)

| Ex. | G' kPa (at 0.001 Hz) | G" | Flexural Strength, MPa | Compressive Strength, MPa | Diametral Tensile Strength, MPa | Flexural Modulus, MPa |
|---|---|---|---|---|---|---|
| 16 | 732 | 358 | 125(14) | 356(6) | 72(11) | 4380(199) |
| 17 | 707 | 363 | 130(15) | 358(11) | 74(5) | 6649(325) |
| 18 | 547 | 264 | 141(11) | 348(7) | 65(5) | 6125(473) |
| 19 | 525 | 257 | 142(8) | 368(11) | 66(6) | 7929(380) |
| 20 | 712 | 349 | 135(14) | 363(10) | 66(13) | 5533(343) |
| 21 | 1377 | 652 | 109(10) | 329(21) | 85(4) | 3348(355) |
| 22 | 416 | 210 | 114(10) | 348(11) | 68(3) | 5098(299) |
| 23 | 1136 | 507 | 105(12) | 350(11) | 64(11) | 5289(251) |
| 24 | 291 | 156 | 131(13) | 317(14) | 82(3) | 9864(454) |
| 25 | 433 | 225 | 155(14) | 407(23) | 82(12) | 12497(421) |
| 26 | 325 | 179 | 136(14) | 374(12) | 62(3) | 11920(574) |
| 27 | 1353 | 630 | 153(18) | 375(13) | 70(7) | 9088(365) |
| 28 | 132 | 81 | 173(15) | 378(14) | 83(8.2) | 10299(786) |
| 29 | 291 | 138 | 172(7) | 385(13) | 93(7) | 10079(477) |
| 30 | 98.5 | 49 | 157(16) | 381(25) | 92(5) | 7604(491) |
| 31 | 180 | 94.4 | 147(13) | 388(19) | 82(9) | 6896(392) |
| 32 | 146 | 73.6 | 151(7) | 352(16) | 80(10) | 7547(403) |

TABLE 5-continued

| Example | G' kPa (at 0.01 Hz) | G'' kPa (at 0.01 Hz) | Melting Point Range (° C.) (Peak Exotherm (° C.)) | Crystalline Component (at 22° C.) |
|---|---|---|---|---|
| 14 | NM | NM | 29-43 (36.9) | Yes |
| 24 | NM | NM | Broadly from 0-35 (no peak) | Yes |
| 25 | NM | NM | Broadly from 0-35 (no peak) | Yes |
| 26 | NM | NM | Broadly from 0-35 (no peak) | Yes |
| TRIAD | 79.5 | 48.8 | No Melting Point | No |
| PRODIGY | 83.3 | 41.7 | No Melting Point | No |
| SUREFIL | 594 | 257 | 7-16 (11) | No |
| REVOTEK** | 883 | 437 | 32-75 (65.0) | Yes |

*NM - Not Measured
**REVOTEK was further determined to contain 23% by weight inorganic filler using standard analytical techniques, i.e., a weighed sample was placed in a crucible, reduced to ash with a Bunsen burner, and the remaining residue weighed.

Additionally, Examples 28-32 were shown to be packable composite materials when evaluated according to the Pre-Cure Composite Packability Test Method described herein. Commercial materials SUREFIL Restorative and PRODIGY Condensable Composite were also evaluated by the same Packability Test Method and determined to be packable composite materials.

Sample Evaluation

Example 15

The composite sample from Example 15 was evaluated for post-cure flexural strength and flexural modulus according to the Test Method described herein. Following curing the resulting hard, tough material had the following flexural strength and modulus values that were very acceptable for a material to be used as a dental article, e.g., as a dental impression tray. Flexural Strength=66 MPa (Standard Deviation=5) and Flexural Modulus=915 MPa (Standard Deviation=115).

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. A dental product comprising a hardenable composition, wherein the hardenable composition comprises:
   a resin system comprising a crystalline resin component;
   greater than 60 wt-% of a filler system; and
   an initiator system;
   wherein the hardenable composition is in the form of a hardenable self-supporting structure having a first shape and sufficient malleability to be formed into a second shape at a temperature of about 15° C. to 38° C.; and
   wherein the crystalline resin component is a polymeric material having crystallizable pendant moieties and the following general formula:

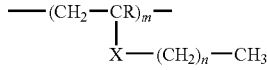

wherein R is hydrogen or a $(C_1\text{-}C_4)$alkyl group, X is —$CH_2$—, —C(O)O—, —O—C(O)—, —C(O)—NH—, —HN—C(O)—, —O—, —NH—, —O—C(O)—NH—, —HN—C(O)—O—, —HN—C(O)—NH—, or —Si(CH$_3$)$_2$—, m is the number of repeating units in the polymer, and n is great enough to provide sufficient side chain length and conformation to form polymers containing crystalline domains or regions;
   with the proviso that if the filler system comprises fibers, the fibers are present in an amount of less than 20 wt-%, based on the total weight of the composition.

2. A dental product comprising a hardenable composition, wherein the hardenable composition comprises:
   a resin system comprising a crystalline resin component;
   greater than 60 wt-% of a filler system; and
   an initiator system;
   wherein the hardenable composition is in the form of a hardenable self-supporting structure having a first shape and sufficient malleability to be formed into a second shape at a temperature of about 15° C. to 38° C.; and
   wherein the filler system comprises an inorganic material comprising nanoscopic particles;
   with the proviso that if the filler system comprises fibers, the fibers are present in an amount of less than 20 wt-%, based on the total weight of the composition.

3. The dental product of claim 2 wherein the inorganic material comprises surface hydroxyl groups.

4. A dental product comprising a hardenable composition, wherein the hardenable composition comprises:
   a resin system comprising a crystalline resin component;
   greater than 60 wt-% of a filler system; and
   an initiator system;
   a surfactant system;
   wherein the hardenable composition is in the form of a hardenable self-supporting structure having a first shape and sufficient malleability to be formed into a second shape at a temperature of about 15° C. to 38° C.;
   with the proviso that if the filler system comprises fibers, the fibers are present in an amount of less than 20 wt-%, based on the total weight of the composition.

5. A dental product comprising a hardenable composition, wherein the hardenable composition comprises:
   a resin system comprising a crystalline resin component;
   greater than 60 wt-% of a filler system; and
   an initiator system;
   wherein the hardenable composition is in the form of a hardenable self-supporting structure having a first shape and sufficient malleability to be formed into a second shape at a temperature of about 15° C. to 38° C.; and
   wherein the hardenable composition has a G' value of about 100 kPa to about 50,000 kPa at a frequency of about 0.005 Hz;
   with the proviso that if the filler system comprises fibers, the fibers are present in an amount of less than 20 wt-%, based on the total weight of the composition.

6. A dental product comprising a hardenable composition, wherein the hardenable composition comprises:
   a resin system comprising a crystalline resin component;
   greater than 60 wt-% of a filler system; and
   an initiator system;

wherein the hardenable composition is in the form of a hardenable self-supporting structure having a first shape and sufficient malleability to be formed into a second shape at a temperature of about 15° C. to 38° C.; and wherein the crystalline resin component has a dendritic, hyperbranched, or a star-shaped structure;

with the proviso that if the filler system comprises fibers, the fibers are present in an amount of less than 20 wt-%, based on the total weight of the composition.

7. A dental product comprising a hardenable composition, wherein the hardenable composition comprises:

a resin system comprising a crystalline resin component;

a filler system comprising inorganic nanoscopic particles having an average primary particle size of no greater than about 50 nm;

a surfactant system; and an initiator system;

wherein the hardenable composition is in the form of a hardenable self-supporting structure having a first shape and sufficient malleability to be formed into a second shape.

8. The dental product of claim 7 which is a preformed crown, a preformed inlay, a preformed onlay, a preformed bridge, a preformed veneer, a preformed orthodontic appliance, a preformed maxillofacial prosthesis, a preformed tooth facsimile, or a preformed tooth splint.

9. The dental product of claim 7 which is a filling material.

10. A dental product comprising a hardenable composition, wherein the hardenable composition comprises:

a resin system comprising a crystalline resin component;

greater than 60 wt-% of a filler system; and an initiator system;

wherein the hardenable composition is in the form of a hardenable self-supporting structure having a first shape and sufficient malleability to be formed into a second shape at a temperature of about 15° C. to 38° C.;

with the proviso that if the filler system comprises fibers, the fibers are present in an amount of less than 20 wt-%, based on the total weight of the composition;

wherein the dental product is a preformed crown, a preformed inlay, a preformed onlay, a preformed bridge, a preformed veneer, a preformed maxillofacial prosthesis, a preformed tooth facsimile, or a preformed tooth splint; and wherein the crystalline resin component comprises polyesters, polyethers, polyolefins, polythioethers, polyarylalkylenes, polysilanes, polyamides, polyurethanes, or combinations thereof.

11. A dental product comprising a hardenable composition, wherein the hardenable composition comprises:

a resin system comprising a crystalline resin component;

greater than 60 wt-% of a filler system; and an initiator system;

wherein the hardenable composition is in the form of a hardenable self-supporting structure having a first shape and sufficient malleability to be formed into a second shape at a temperature of about 15° C. to 38° C.; and wherein the crystalline resin component comprises polyesters, polyethers, polyolefins, polythioethers, polyarylalkylenes, polysilanes, polyamides, polyurethanes, or combinations thereof;

with the proviso that if the filler system comprises fibers, the fibers are present m an amount of less than 20 wt-%, based on the total weight of the composition.

12. The dental product of claim 7 wherein the filler system is present in an amount greater than 50 wt-%, based on the total weight of the composition.

13. The dental product of claim 7 wherein the hardenable self-supporting structure having a first shape has sufficient malleability to be formed into a second shape at a temperature of about 15° C. to 38° C.

14. The dental product of claim 13 wherein the hardenable self-supporting structure having a first shape has sufficient malleability to be formed into a second shape substantially similar to the first shape.

15. The dental product of claim 7 wherein if the filler system comprises fibers, the fibers are present in an amount of less than 20 wt-%, based on the total weight of the composition.

16. The dental product of claim 7 wherein the resin system further comprises a noncrystalline resin component.

17. The dental product of claim 7 wherein the crystalline resin component has a dendritic, hyperbranched, or a star-shaped structure.

18. The dental product of claim 7 wherein upon hardening the structure in the second shape, the hardened structure has a flexural strength of at least about 25 MPa.

19. The dental product of claim 10 wherein the hardenable composition has a sufficient malleability to be formed into a second shape at room temperature.

20. The dental product of claim 10 wherein the filler system is greater than 70 wt-%.

21. The dental product of claim 10 wherein at least a portion of the filler system comprises particulate filler.

22. The dental product of claim 10 wherein upon hardening the structure in the second shape, the hardened structure has a flexural strength of at least about 25 MPa.

23. The dental product of claim 10 wherein the crystalline resin component comprises a reactive group.

24. The dental product of claim 11 wherein upon hardening the structure in the second shape, the hardened structure does not require an additional veneering material for the hardened dental product.

25. The dental product of claim 24 wherein the crystalline resin component comprises saturated, linear, aliphatic polyester polyols containing primary hydroxyl end groups.

26. The dental product of claim 25 wherein the hydroxyl end groups are modified to introduce polymerizable unsaturated functional groups.

27. A dental impression tray comprising a hardenable composition, wherein the hardenable composition comprises:

a resin system comprising a crystalline resin component;

a filler system comprising inorganic nanoscopic particles having an average primary particle size of no greater than about 50 nm;

a surfactant system; and an initiator system;

wherein the hardenable composition is in the form of a hardenable self-supporting structure having a first shape and sufficient malleability to be formed into a second shape.

28. The dental impression tray of claim 27 wherein the self-supporting structure has at least one structured surface.

29. The dental impression tray of claim 28 wherein the structured surface is formed by a porous substrate.

30. The dental impression tray of claim 28 wherein the structured surface is a microreplicated surface.

31. A preformed dental crown comprising a composition comprising a resin system, a filler system, and an imtiator system;

wherein the resin system comprises a crystalline resin component;

wherein the composition is in the form of a hardenable self-supporting structure having a first shape and sufficient malleability to be formed into a second shape; and
wherein the hardenable self-supporting structure having a first shape has sufficient malleability to be formed into a second shape at a temperature of about 15° C. to 38° C.

32. The preformed dental crown of claim 31 wherein the filler system is present in an amount greater than 60 wt-%, based on the total weight of the composition.

33. The preformed dental crown of claim 31 wherein the filler system is present in an amount greater than 70 wt-%, based on the total weight of the composition.

34. The preformed dental crown of claim 31 wherein upon forming the second shape and hardening the structure in the second shape, the hardened structure does not need an additional veneering material.

35. The preformed dental crown of claim 31 which is in packaging.

36. The preformed dental crown of claim 35 wherein the packaging is light-blocking packaging sufficient to protect the preformed dental crown from conditions that would activate the initiator system and cause premature hardening.

37. The preformed dental crown of claim 31 further comprising a resin material lining the crown.

38. The preformed dental crown of claim 31 wherein the resin system comprises a compound of the formula:

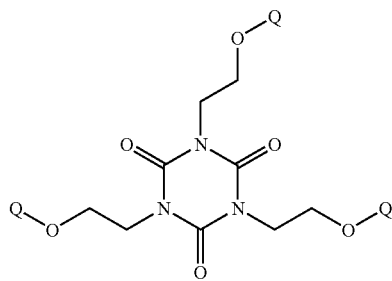

wherein each Q independently comprises polyester segments, polyamide segments, polyurethane segments, polyether segments, or combinations thereof.

39. The dental product of claim 10 wherein the crystalline resin component comprises saturated, linear, aliphatic polyester polyols containing primary hydroxyl end groups.

40. The dental product of claim 39 wherein the hydroxyl end groups are modified to introduce polymerizable unsaturated functional groups.

41. A dental product comprising a hardenable composition, wherein the hardenable composition comprises:
a resin system comprising a crystalline resin component;
greater than 60 wt-% of a filler system; and
an initiator system;
wherein the hardenable composition is in the form of a hardenable self-supporting structure having a first shape and sufficient malleability to be formed into a second shape at a temperature of about 15° C. to 38° C.;
with the proviso that if the filler system comprises fibers, the fibers are present in an amount of less than 20 wt-%, based on the total weight of the composition;
wherein the dental product is a preformed crown, a preformed inlay, a preformed onlay, a preformed bridge, a preformed veneer, a preformed maxillofacial prosthesis, a preformed tooth facsimile, or a preformed tooth splint; and wherein the crystalline resin component is a polymeric material having crystallizable pendant moieties and the following general formula:

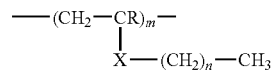

wherein R is hydrogen or a $(C_1-C_4)$alkyl group, X is —$CH_2$—, —C(O)O—, —O—C(O)—, —C(O)—NH—, —HN—C(O)—, —O—, —NH—, —O—C(O)—NH—, —HN—C(O)—O—, —HN—C(O)—NH—, or —Si($CH_3$)$_2$—, m is the number of repeating units in the polymer, and n is great enough to provide sufficient side chain length and conformation to form polymers containing crystalline domains or regions.

42. A dental product comprising a hardenable composition, wherein the hardenable composition comprises:
a resin system comprising a crystalline resin component;
greater than 60 wt-% of a filler system; and
an initiator system;
wherein the hardenable composition is in the form of a hardenable self-supporting structure having a first shape and sufficient malleability to be formed into a second shape at a temperature of about 15° C. to 38° C.;
with the proviso that if the filler system comprises fibers, the fibers are present in an amount of less than 20 wt-%, based on the total weight of the composition;
wherein the dental product is a preformed crown, a preformed inlay, a preformed onlay, a preformed bridge, a preformed veneer, a preformed maxillofacial prosthesis, a preformed tooth facsimile, or a preformed tooth splint; and
wherein the filler system comprises an inorganic material comprising nanoscopic particles.

43. The dental product of claim 42 wherein the inorganic material comprises surface hydroxyl groups.

44. A dental product comprising a hardenable composition, wherein the hardenable composition comprises:
a resin system comprising a crystalline resin component;
greater than 60 wt-% of a filler system; and
an initiator system;
wherein the hardenable composition is in the form of a hardenable self-supporting structure having a first shape and sufficient malleability to be formed into a second shape at a temperature of about 15° C. to 38° C.;
with the proviso that if the filler system comprises fibers, the fibers are present in an amount of less than 20 wt-%, based on the total weight of the composition;
wherein the dental product is a preformed crown, a preformed inlay, a preformed onlay, a preformed bridge, a preformed veneer, a preformed maxillofacial prosthesis, a preformed tooth facsimile, or a preformed tooth splint; and
wherein the hardenable composition further comprises a surfactant system.

45. A dental product comprising a hardenable composition, wherein the hardenable composition comprises:
a resin system comprising a crystalline resin component;
greater than 60 wt-% of a filler system; and
an initiator system;
wherein the hardenable composition is in the form of a hardenable self-supporting structure having a first shape and sufficient malleability to be formed into a second shape at a temperature of about 15° C. to 38° C.;

with the proviso that if the filler system comprises fibers, the fibers are present in an amount of less than 20 wt-%, based on the total weight of the composition;

wherein the dental product is a preformed crown, a preformed inlay, a preformed onlay, a preformed bridge, a preformed veneer, a preformed maxillofacial prosthesis, a preformed tooth facsimile, or a preformed tooth splint; and wherein the hardenable composition has a G' value of about 100 kPa to about 50,000 kPa at a frequency of about 0.005 Hz.

46. A dental product comprising a hardenable composition, wherein the hardenable composition comprises:

a resin system comprising a crystalline resin component;
greater than 60 wt-% of a filler system; and
an initiator system;

wherein the hardenable composition is in the form of a hardenable self-supporting structure having a first shape and sufficient malleability to be formed into a second shape at a temperature of about 15° C. to 38° C.;

with the proviso that if the filler system comprises fibers, the fibers are present in an amount of less than 20 wt-%, based on the total weight of the composition;

wherein the dental product is a preformed crown, a preformed inlay, a preformed onlay, a preformed bridge, a preformed veneer, a preformed maxillofacial prosthesis, a preformed tooth facsimile, or a preformed tooth splint; and wherein the crystalline resin component has a dendritic, hyperbranched, or a star-shaped structure.

47. The dental product of claim 24 wherein the dental product is a preformed crown, a preformed inlay, a preformed onlay, a preformed bridge, a preformed veneer, a preformed orthodontic appliance, a preformed maxillofacial prosthesis, a preformed tooth facsimile, or a preformed tooth splint.

48. The dental product of claim 24 which is a filling material.

49. The dental product of claim 24 which is a dental impression tray.

50. The dental product of claim 1 wherein the dental product is a preformed crown, a preformed inlay, a preformed onlay, a preformed bridge, a preformed veneer, a preformed orthodontic appliance, a preformed maxillofacial prosthesis, a preformed tooth facsimile, or a preformed tooth splint.

51. The dental product of claim 1 which is a filling material.

52. The dental product of claim 1 which is a dental impression tray.

53. The dental product of claim 2 wherein the dental product is a preformed crown, a preformed inlay, a preformed onlay, a preformed bridge, a preformed veneer, a preformed orthodontic appliance, a preformed maxillofacial prosthesis, a preformed tooth facsimile, or a preformed tooth splint.

54. The dental product of claim 2 which is a filling material.

55. The dental product of claim 2 which is a dental impression tray.

56. The dental product of claim 4 wherein the dental product is a preformed crown, a preformed inlay, a preformed onlay, a preformed bridge, a preformed veneer, a preformed orthodontic appliance, a preformed maxillofacial prosthesis, a preformed tooth facsimile, or a preformed tooth splint.

57. The dental product of claim 4 which is a filling material.

58. The dental product of claim 4 which is a dental impression tray.

59. The dental product of claim 5 wherein the dental product is a preformed crown, a preformed inlay, a preformed onlay, a preformed bridge, a preformed veneer, a preformed orthodontic appliance, a preformed maxillofacial prosthesis, a preformed tooth facsimile, or a preformed tooth splint.

60. The dental product of claim 5 which is a filling material.

61. The dental product of claim 5 which is a dental impression tray.

62. The dental product of claim 6 wherein the dental product is a preformed crown, a preformed inlay, a preformed onlay, a preformed bridge, a preformed veneer, a preformed orthodontic appliance, a preformed maxillofacial prosthesis, a preformed tooth facsimile, or a preformed tooth splint.

63. The dental product of claim 6 which is a filling material.

64. The dental product of claim 6 which is a dental impression tray.

* * * * *

UNITED STATES PATENT AND TRADEMARK OFFICE
CERTIFICATE OF CORRECTION

PATENT NO. : 7,674,850 B2  Page 1 of 1
APPLICATION NO. : 10/219398
DATED : March 9, 2010
INVENTOR(S) : Karim et al.

It is certified that error appears in the above-identified patent and that said Letters Patent is hereby corrected as shown below:

In column 9, line 40, delete "dimetliacrylate" and insert --dimethacrylate--;

In column 37, line 63, claim 11, delete "m" and insert --an--;

In column 38, line 38, claim 25, delete "claim 24" and insert --claim 11--;

In column 38, line 64, claim 31, delete "imtiator" and insert --initiator--;

In column 41, line 31, claim 47, delete "claim 24" and insert --claim 11--;

In column 41, line 36, claim 48, delete "claim 24" and insert --claim 11--;

In column 41, line 38, claim 49, delete "claim 24" and insert --claim 11--.

Signed and Sealed this

Seventh Day of September, 2010

David J. Kappos
*Director of the United States Patent and Trademark Office*